United States Patent
Zhu et al.

(10) Patent No.: US 11,867,627 B2
(45) Date of Patent: Jan. 9, 2024

(54) COMPACT GUIDED DIFFUSE OPTICAL TOMOGRAPHY SYSTEM FOR IMAGING A LESION REGION

(71) Applicants: Quing Zhu, St. Louis, MO (US); Hamed Vavadi, St. Louis, MO (US); Atahar Mostafa, St. Louis, MO (US)

(72) Inventors: Quing Zhu, St. Louis, MO (US); Hamed Vavadi, St. Louis, MO (US); Atahar Mostafa, St. Louis, MO (US)

(73) Assignees: Washington University, St. Louis, MO (US); The University of Connecticut, Farmington, CT (US)

( * ) Notice: Subject to any disclaimer, the term of this patent is extended or adjusted under 35 U.S.C. 154(b) by 562 days.

(21) Appl. No.: 16/599,322

(22) Filed: Oct. 11, 2019

(65) Prior Publication Data
US 2020/0116630 A1    Apr. 16, 2020

Related U.S. Application Data

(60) Provisional application No. 62/745,080, filed on Oct. 12, 2018.

(51) Int. Cl.
*G01N 21/47*    (2006.01)
*G01N 21/63*    (2006.01)
(Continued)

(52) U.S. Cl.
CPC ....... *G01N 21/4795* (2013.01); *G01N 21/636* (2013.01); *G06T 11/006* (2013.01);
(Continued)

(58) Field of Classification Search
CPC ............. G01N 21/4795; G01N 21/636; G01N 2021/1787; G01N 2201/0612; G01N 21/474; G06T 11/006; A61B 5/0073
See application file for complete search history.

(56) References Cited

U.S. PATENT DOCUMENTS 6,264,610 B1 * 7/2001 Zhu .................... A61B 5/0091
                                                     600/443
6,956,650 B2   10/2005 Boas et al.
(Continued)

FOREIGN PATENT DOCUMENTS

CN    201699203 U  *  1/2011   ............. H01R 13/02
CN    101963651 B  *  2/2015   ......... G01R 31/2805
(Continued)

*Primary Examiner* — Mohamed K Amara
(74) *Attorney, Agent, or Firm* — Armstrong Teasdale LLP

(57) ABSTRACT

A compact diffuse optical tomography system for generating a functional image of a lesion region is provided. The system includes a source subsystem, a probe, a detection subsystem, and a computing device. The source subsystem includes laser diodes and a laser diode driver board. The probe is configured to emit the optical waves generated by the source subsystem toward the lesion region and detect optical waves reflected by the lesion region. The detection subsystem includes a miniaturized detection board and a miniaturized data acquisition board. The miniaturized detection board includes a photomultiplier tube configured to convert the optical waves detected by the probe to electrical signals. The miniaturized data acquisition board is configured to convert electrical signals outputted by the miniaturized detection board to digital signals. The computing device is configured to receive the digital signals, reconstruct the functional image, and display the functional image.

20 Claims, 22 Drawing Sheets
(16 of 22 Drawing Sheet(s) Filed in Color)

(51) Int. Cl.
  *G06T 11/00* (2006.01)
  *G01N 21/17* (2006.01)
  *A61B 5/00* (2006.01)

(52) U.S. Cl.
  CPC .... *A61B 5/0073* (2013.01); *G01N 2021/1787* (2013.01); *G01N 2201/0612* (2013.01)

(56) References Cited

U.S. PATENT DOCUMENTS

| | | | |
|---|---|---|---|
| 7,107,116 B2 | 9/2006 | Geng | |
| 7,615,009 B2* | 11/2009 | Koste | H04B 10/505 |
| | | | 600/443 |
| 7,729,750 B2* | 6/2010 | Tromberg | G01N 21/6456 |
| | | | 356/318 |
| 7,983,740 B2* | 7/2011 | Culver | A61B 5/0073 |
| | | | 600/476 |
| 9,134,229 B2 | 9/2015 | Lesage et al. | |
| 9,557,154 B2* | 1/2017 | Tearney | G01B 9/02091 |
| 9,687,157 B2* | 6/2017 | Wax | G01J 3/45 |
| 9,867,542 B2 | 1/2018 | Wu et al. | |
| 9,927,362 B2 | 3/2018 | Kumar et al. | |
| 9,964,747 B2 | 5/2018 | Ntziachristos et al. | |
| 10,321,896 B2* | 6/2019 | Herzog | G06T 7/30 |
| 10,349,836 B2* | 7/2019 | Herzog | A61B 8/4281 |
| 10,354,379 B2* | 7/2019 | Zalev | A61B 5/0095 |
| 10,888,304 B2* | 1/2021 | O'Donnell | A61B 5/0095 |
| 10,901,074 B1* | 1/2021 | Pan | G01S 17/89 |
| 10,969,405 B2* | 4/2021 | Shetty | G01N 21/31 |
| 11,743,741 B1* | 8/2023 | Pulido Mancera | H04W 16/18 |
| | | | 455/456.1 |
| 2007/0073122 A1* | 3/2007 | Hoarau | A61B 5/6826 |
| | | | 600/323 |
| 2008/0058638 A1* | 3/2008 | Zhu | G01N 21/6428 |
| | | | 600/425 |
| 2008/0123083 A1* | 5/2008 | Wang | A61B 5/0091 |
| | | | 356/73 |
| 2009/0002685 A1* | 1/2009 | Fukutani | A61B 5/0073 |
| | | | 181/141 |
| 2009/0054763 A1* | 2/2009 | Wang | A61B 8/14 |
| | | | 600/453 |
| 2009/0257464 A1* | 10/2009 | Dantus | G01B 9/02091 |
| | | | 372/33 |
| 2010/0094134 A1* | 4/2010 | Zhu | A61B 8/4416 |
| | | | 600/473 |
| 2010/0208965 A1 | 8/2010 | Jiang et al. | |
| 2010/0243916 A1* | 9/2010 | Maurer | G01J 3/0289 |
| | | | 250/237 G |
| 2010/0265493 A1* | 10/2010 | Jiang | G01N 21/4795 |
| | | | 356/51 |
| 2011/0137177 A1* | 6/2011 | Toma | A61B 8/00 |
| | | | 600/473 |
| 2013/0190595 A1* | 7/2013 | Oraevsky | A61B 5/0035 |
| | | | 600/407 |
| 2014/0236021 A1* | 8/2014 | Islam | A61B 5/0091 |
| | | | 600/475 |
| 2015/0066436 A1 | 3/2015 | Elliott et al. | |
| 2015/0101411 A1 | 4/2015 | Zalev et al. | |
| 2016/0282432 A1 | 9/2016 | Wang | |
| 2016/0287211 A1* | 10/2016 | DaCosta | A61B 8/48 |
| 2017/0000353 A1* | 1/2017 | Li | A61B 1/0615 |
| 2018/0064347 A1* | 3/2018 | Adair | A61B 5/0035 |
| 2020/0145065 A1* | 5/2020 | Ashrafi | H04B 7/10 |
| 2020/0288982 A1* | 9/2020 | Islam | A61B 5/0088 |
| 2022/0047161 A1* | 2/2022 | Zhu | A61B 5/0073 |
| 2023/0006719 A1* | 1/2023 | Ashrafi | H04B 7/0413 |

FOREIGN PATENT DOCUMENTS

| | | | | |
|---|---|---|---|---|
| CN | 102077108 B | * | 2/2015 | G01R 33/54 |
| CN | 106251313 A | * | 12/2016 | A61B 6/037 |
| WO | WO-2011077203 A2 | * | 6/2011 | A61B 5/0059 |
| WO | WO-2017160889 A1 | * | 9/2017 | A62B 17/15 |
| WO | 2018054444 A1 | | 3/2018 | |

* cited by examiner (b) 780 nm

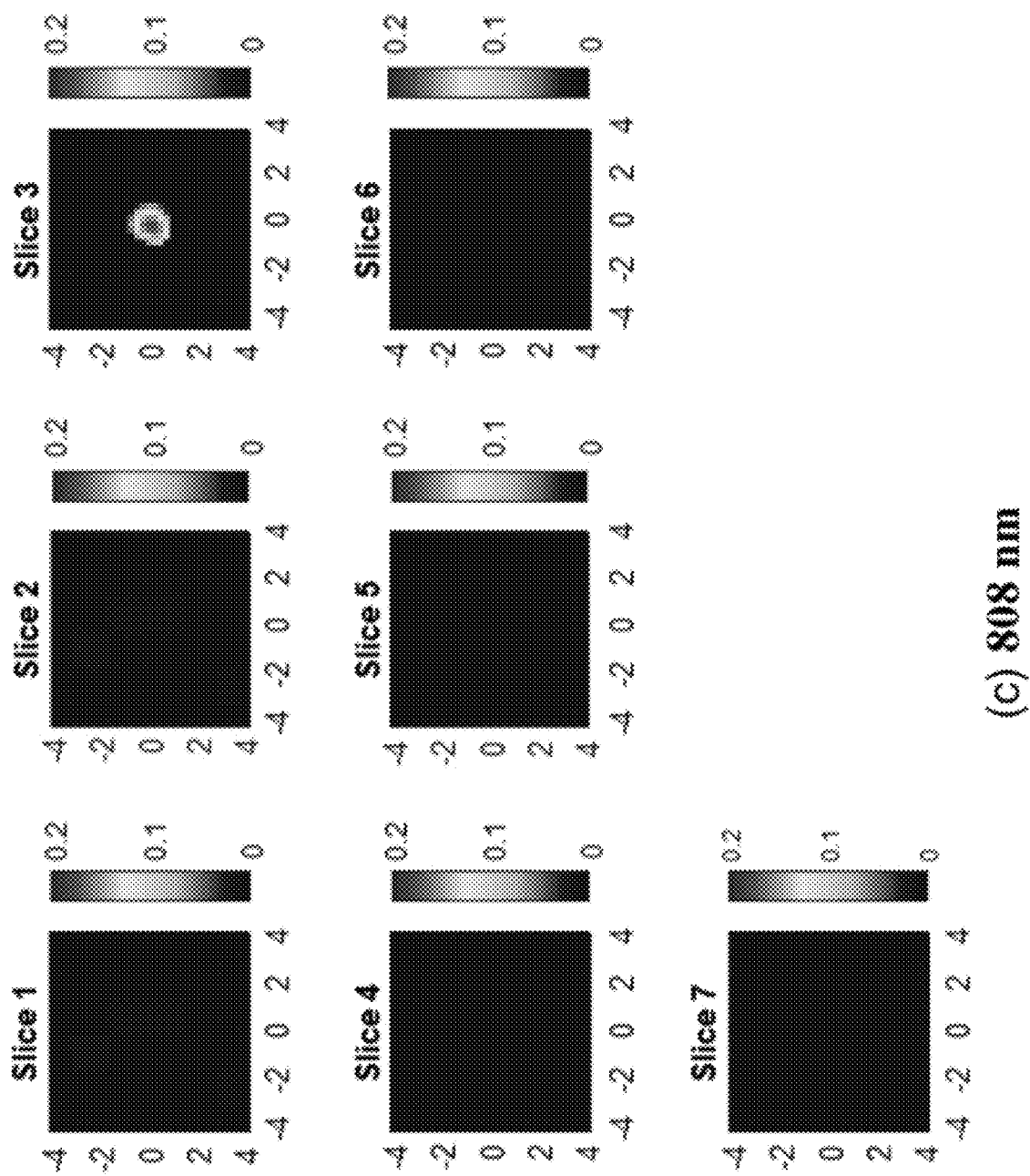

COMPACT GUIDED DIFFUSE OPTICAL TOMOGRAPHY SYSTEM FOR IMAGING A LESION REGION

CROSS-REFERENCE TO RELATED APPLICATION

This application claims the benefit of U.S. Provisional Application Ser. No. 62/745,080, filed Oct. 12, 2018, entitled "A COMPACT ULTRASOUND-GUIDED DIFFUSE OPTICAL SYSTEM FOR BREAST CANCER IMAGING," which is hereby incorporated in its entirety herein.

GOVERNMENTAL SUPPORT

This invention was made with government support under grant number R01EB002136 awarded by National Institutes of Health. The government has certain rights in the invention.

BACKGROUND

The field of the disclosure relates generally to imaging systems and methods, and more particularly to compact guided diffuse optical tomography (DOT) systems for imaging a lesion region of a subject.

Breast cancer is the most common cancer among women and is expected to account for 29% of all new cancer diagnoses in women in 2018. Based on the statistics from American cancer society, there are around 2.8 million women with a history of breast cancer in the United States. In 2018, 266,120 new cases of invasive breast cancer along with 63,960 new cases of noninvasive breast cancer are expected to be detected in the U.S. Despite the decrease in death rates for breast cancer since 1989, it is estimated that about 40,920 women in the U.S. may have died in 2018 from breast cancer. Currently, many patients with invasive breast cancer undergo neoadjuvant treatment with chemotherapy or endocrine therapy. Locally advanced malignancy that substantially responds to neoadjuvant therapy may become amenable to breast conserving treatment. Neoadjuvant therapy affords the oncologist an opportunity to assess the in-vivo response to a specific treatment regimen and also provides important prognostic information. In particular, patients who achieved a pathological complete response (pCR) show improved survival rates as compared to those who did not respond completely.

Different modalities have been used to assess a patient's response to a neoadjuvant therapy. Ultrasound (US) and mammography show moderate sensitivity in the assessment of tumor response. Dynamic contrast-enhanced MRI and 18F-fluorodeoxyglucose positron emission tomography/computed tomography (PET/CT) have been used to predict breast cancer response to neoadjuvant therapy, and have shown capability in early identification of response. However, MRI and PET/CT are expensive and require injection of contrast agents. The repeated use of these modalities in monitoring patients during treatment is, therefore, not feasible.

Near-infrared (NIR) diffuse optical tomography (DOT) is a noninvasive imaging technique that uses NIR light to estimate optical properties of tissue. Because of the minimal absorption of water in the NIR spectrum (from approximately 700 to approximately 900 nm), light penetrates several centimeters into tissue. Within the NIR spectrum, oxygenated and deoxygenated hemoglobin ($HbO_2$ and $Hb$) are major chromophores absorbing light and can be used to characterize tumor vasculature, which is directly related to tumor angiogenesis. DOT systems are usually portable, require no contrast agents, and have relatively low cost. These excellent features make DOT systems an ideal modality for diagnosis of breast cancer and for assessment of neoadjuvant treatment response. However, known DOT systems have a relatively low signal-to-noise ratio and are still relatively bulky.

BRIEF DESCRIPTION

In one aspect, a compact diffuse optical tomography (DOT) system for generating a functional image of a lesion region of a subject is provided. The system includes a source subsystem, a probe, a detection subsystem, and a computing device. The source subsystem includes a plurality of laser diodes configured to generate near-infrared (NIR) optical waves and a laser diode driver board configured to drive the plurality of laser diodes. The probe is configured to emit the optical waves generated by the source subsystem toward the lesion region and configured to detect optical waves reflected by the lesion region. The detection subsystem includes a miniaturized detection board and a miniaturized data acquisition (DAQ) board. The miniaturized detection board includes a photomultiplier tube (PMT), wherein the PMT has a plurality of channels and configured to convert the optical waves detected by the probe to electrical signals. The miniaturized detection board further includes a combined board formed as one single board and including a frequency mixer, a second-stage amplifier, and a bandpass filter. The frequency mixer is configured to mix the electrical signals with reference signals to derive mixed signals. The second-stage amplifier is configured to amplify the mixed signals to derive amplified signals. The bandpass filter is configured to filter the amplified signals to derive electrical signals of a selected frequency outputted by the miniaturized detection board. The miniaturized DAQ board is configured to convert the electrical signals outputted by the miniaturized detection board to digital signals. The computing device is configured to receive the digital signals sent from the detection subsystem, reconstruct the functional image of the lesion region based on the digital signals, and display the functional image.

In another aspect, a compact DOT system for generating a functional image of a lesion region of a subject is provided. The system includes a source subsystem, a probe, a detection subsystem, and a computing device. The source subsystem includes a plurality of laser diodes configured to generate NIR optical waves, and a laser diode driver board configured to drive the plurality of laser diodes. The probe is configured to emit the optical waves generated by the source subsystem toward the lesion region and configured to detect optical waves reflected by the lesion region. The detection subsystem includes a miniaturized detection board and a miniaturized DAQ board. The miniaturized detection board includes a PMT having a plurality of channels and configured to convert the optical waves detected by the probe to electrical signals. The miniaturized DAQ board is configured to convert electrical signals outputted by the miniaturized detection board to digital signals. The computing device is configured to receive the digital signals sent from the detection subsystem, reconstruct the functional image of the lesion region based on the digital signals, and display the functional image.

In yet another aspect, a compact DOT system for generating a functional image of a lesion region of a subject is provided. The system includes a source subsystem, a probe, a detection subsystem, and a computing device. The source subsystem includes a plurality of laser diodes configured to generate NIR optical waves, and a laser diode driver board configured to drive the plurality of laser diodes, wherein the laser diode driver board includes one or more optical switches configured to multiplex the optical waves generated by the plurality of laser diodes. The probe is configured to emit the optical waves generated by the source subsystem toward the lesion region and configured to detect optical waves reflected by the lesion region. The detection subsystem includes a miniaturized detection board and a miniaturized DAQ board. The miniaturized detection board includes a PMT having a plurality of channels and configured to convert the optical waves detected by the probe to electrical signals. The miniaturized DAQ board is configured to convert electrical signals outputted by the miniaturized detection board to digital signals. The computing device is configured to receive the digital signals sent from the detection subsystem, reconstruct the functional image of the lesion region based on the digital signals, and display the functional image.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The drawings described below illustrate various aspects of the disclosure.

FIG. 5C shows absorption maps of the phantom used for FIG. 5A, where the maps are measured with the DOT system shown in FIG. 3 with the optical waves having a wavelength of 808 nm.

DETAILED DESCRIPTION

The systems and methods described herein relate to imaging systems and methods, and more specifically, a compact diffuse optical tomography (DOT) system used to generate functional images of a lesion region in a subject. A subject as used herein is a human (live or deceased), an animal (live or deceased), an organ or part of an organ of a human or an animal, or part of a human or an animal. For example, a subject may be a breast, part of a human that includes an ovary, or part of a human that includes the colon or part of the colon. A lesion includes abnormal tissue in a subject, such as a tumor, benign or malignant. A lesion region of a subject includes the region of the subject that includes a lesion. Functional images are images or maps of an imaging volume that includes a lesion region. Functional images may be maps of the optical properties of the voxels of the imaging volume, such as absorption maps of the imaging volume, depicting the absorption coefficient at each voxel. Functional maps may be hemoglobin maps, depicting the hemoglobin concentration at each voxel. Functional maps may also be total hemoglobin concentration (tHb) maps, oxyhemoglobin (oxyHb) maps, or deoxyhemoglobin (deoxyHb) maps, depicting the tHb, oxyHb, or deoxyHb concentration at each voxel, respectively.

To overcome DOT's limitations of low spatial resolution and lesion uncertainty due to intense light scattering in tissue, a DOT guided with a conventional imaging modality has been introduced. The conventional imaging modality locates lesion morphology and guides DOT reconstruction. A US-guided compact DOT system disclosed herein is only one example of a compact DOT system, the DOT system can be guided by other imaging modalities.

Figure 1A:
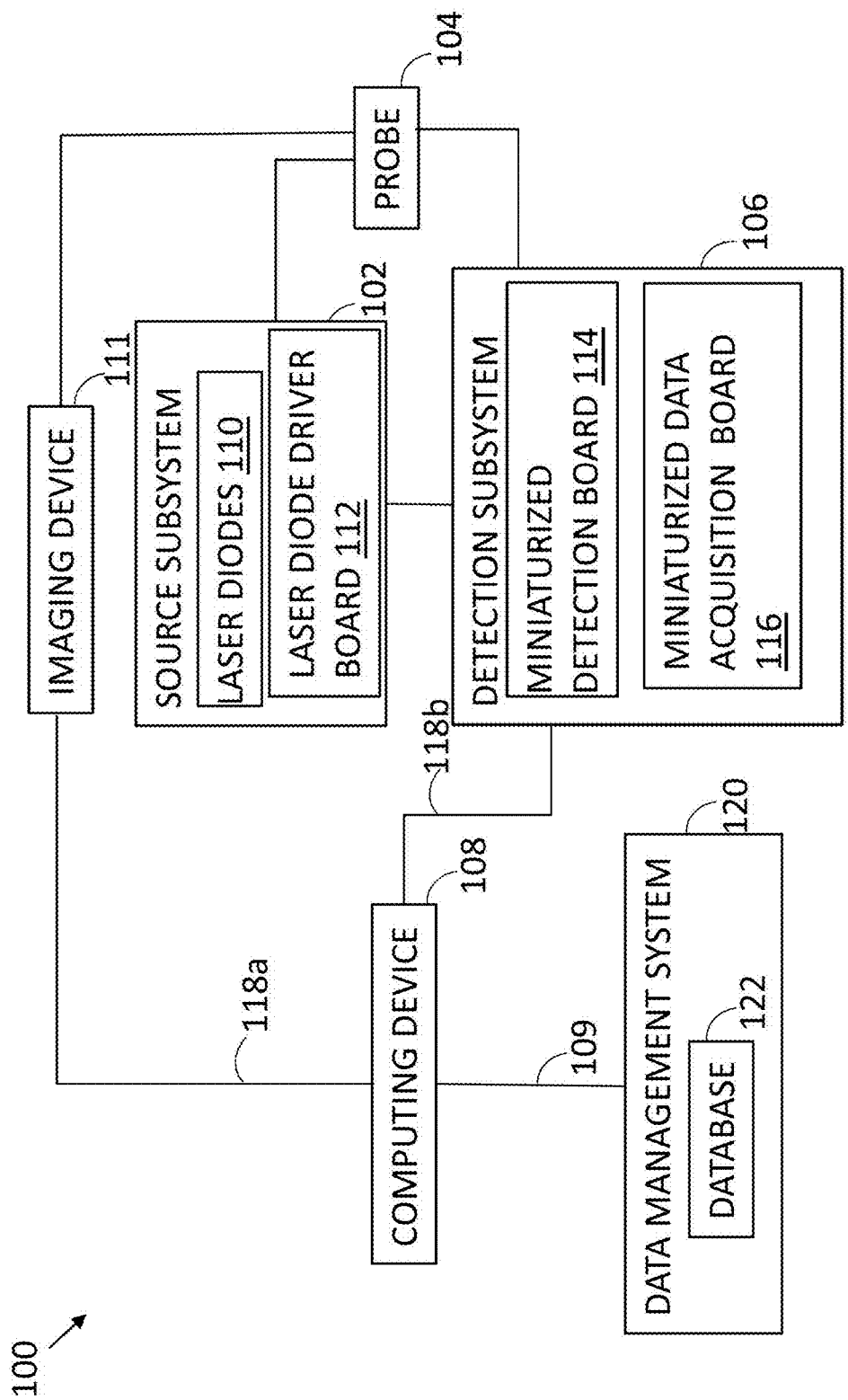
FIG. 1A is a block diagram of an exemplary compact diffuse optical tomography (DOT) system in accordance with an aspect of the disclosure.

The systems and methods disclosed herein have improved signal-to-noise ratios and reduced physical dimensions, and are user-friendly, compared to a known DOT system. FIG. 1A is a block diagram of an exemplary compact DOT system 100. System 100 includes a source subsystem 102, a probe 104, a detection subsystem 106, and a computing device 108. DOT system 100 includes, but not limited to, a near-infrared (NIR) diffuse optical tomography device or an NIR imager. Source subsystem 102 includes a plurality of laser diodes 110 and a laser diode driver board 112. Laser diodes 110 are configured to generate NIR optical waves. Laser diode driver board 112 is configured to drive diodes 110.

Probe 104 is configured to emit the optical waves generated by source subsystem 102 toward a lesion region of the subject. Probe 104 is also configured to detect optical waves reflected by the lesion region.

Figure 1B:
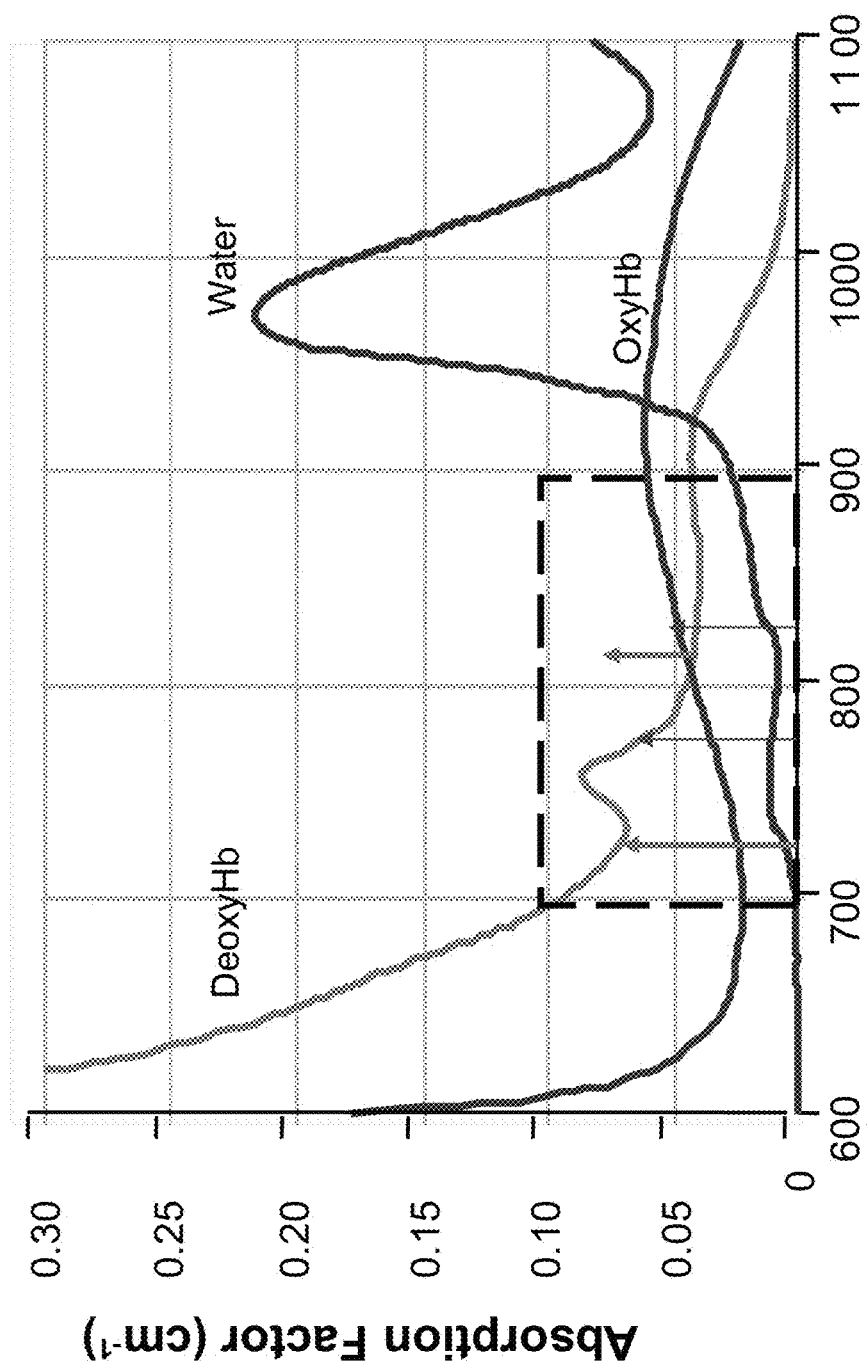
FIG. 1B is plot showing absorption of optical waves at the near infrared spectrum by water, oxyhemoglobin (oxyHb), and deoxyhemoglobin (deoxyHb).

In various embodiments, the light spectrum used in system 100 is at the near-infrared spectrum (wavelength from approximately 700 to approximately 900 nm). NIR DOT imaging is a noninvasive imaging technique that uses NIR light to estimate optical properties of tissue. FIG. 1B shows absorption of light as a function of the wavelength of the light for water (the blue line), oxyhemoglobin (oxyHb) (the dark red line), and deoxyhemoglobin (deoxyHb) (the pink line). The rectangular box indicates the NIR spectrum range. As shown in FIG. 1B, in the NIR spectrum range, water absorbs light much less than oxyHb and deoxyHb, and oxyHb and deoxyHb each absorb light at different rates depending on the wavelength of the emitted light. Four arrows superimposed on FIG. 1B indicate absorption properties at wavelengths of 730 nm, 780 nm, 808 nm, and 830 nm, respectively. Because of the minimal absorption of water in the NIR spectrum, NIR light penetrates several centimeters into tissue. Within the NIR spectrum, oxygenated and deoxygenated hemoglobin are major chromophores absorbing light and can be used to characterize tumor vasculature, which is directly related to tumor angiogenesis.

In the exemplary embodiment, laser diodes 110 are configured to emit optical waves of a plurality of wavelengths toward an imaging volume of the subject. In various embodiments, laser diodes 110 are configured to emit optical waves at wavelengths 730, 780, 808 and 830 nm. The imaging volume includes a lesion region.

In the exemplary embodiment, detection subsystem 106 includes a miniaturized detection board 114 and a miniaturized data acquisition (DAQ) board 116. Miniaturized detection board 114 includes one or more photomultiplier tubes (PMT) configured to convert optical waves detected by probe 104 to electrical signals. Miniaturized DAQ board 116 is configured to convert electrical signals outputted from miniaturized detection board 114 to digital signals. Computing device 108 is configured to receive the digital signals from detection subsystem 106 and reconstruct them into functional image of the lesion region. Computing device 108 is also configured to display the reconstructed functional image. One suitable image reconstruction system and method is disclosed in PCT Application Serial PCT/US2018/057364, filed Oct. 24, 2018, entitled "SYSTEMS AND METHODS OF OPTIMIZING FUNCTIONAL IMAGES OF A LESION REGION USING GUIDED DIFFUSE OPTICAL TOMOGRAPHY", which is incorporated by reference in its entirety. For example, one example image reconstruction method includes receiving, using a computing device, a plurality of measurements from a diffuse optical tomography (DOT) device. The plurality of measurements includes lesion functional data from the lesion region of the breast and reference functional data from a healthy tissue region of a contralateral breast. The method further includes transforming, using the computing device, the lesion functional data and the reference functional data to produce perturbation data. The perturbation data includes a normalized difference between the lesion functional data and the reference functional data. The method also includes generating, using the computing device, a preliminary estimate of the functional image by applying a pseudoinverse matrix of a weight matrix to the perturbation data. The pseudoinverse matrix may a truncated pseudoinverse matrix. The weight matrix includes a plurality of elements representing system measurement sensitivity and distribution of diffused optical waves in a homogenous medium. The method further includes generating, using the computing device, each optimized functional image by iteratively optimizing successive estimates of the functional image regularized by the preliminary estimate of the functional image weighted by a regularization parameter. A value of the optimized functional image at each voxel in the lesion region is indicative of a hemoglobin concentration at that voxel. The method may also include displaying the at least one optimized functional image on a display device. Suitable image reconstruction methods may include more, fewer, and/or different steps.

In operation, optical waves generated by source subsystem 102 are sent to probe 104 and emitted toward a lesion region of the subject via probe 104. Probe 104 detects optical waves reflected by the lesion region. The detected signals are sent to detection subsystem 106 and converted to electrical signals. The electrical signals are then converted to digital signals by miniaturized DAQ board 116. The digital signals are received in computing device 108 and reconstructed into a functional image of the lesion region. The reconstructed image is also displayed by computing device 108.

In various embodiments, system 100 is a guided DOT system. That is, system 100 may further include an imaging device 111 that is configured to acquire guiding data of a subject including the lesion region of the subject. Imaging device 111 may be any suitable imaging device that makes use of an imaging modality different from DOT, including, but not limited to, an ultrasound device, a magnetic resonance imaging system, an x-ray device, or a computed tomography device. In various embodiments, imaging device 111 acquires data also through probe 104 when the imaging modality of imaging device 111 is US.

In the exemplary embodiment, computing device 108 is coupled to imaging device 111 via a data conduit 118a and operatively coupled to detection subsystem 106 via a data conduit 118b. It should be noted that, as used herein, the term "couple" is not limited to a direct mechanical, electrical, and/or communication connection between components, but may also include an indirect mechanical, electrical, and/or communication connection between multiple components. Although one computing device 108 is depicted in FIG. 1A, two or more computing devices may be used in the system. Imaging device 111 and detection subsystem 106 may be in communication with different computing devices (not shown) and the computing devices are in communication with each other.

Imaging device 111 and detection subsystem 106 may communicate with computing device 108 using a wired network connection (e.g., Ethernet or an optical fiber via a universal serial bus port on computing device 108), a wireless communication means, such as radio frequency (RF), e.g., FM radio and/or digital audio broadcasting, an Institute of Electrical and Electronics Engineers (IEEE®) 802.11 standard (e.g., 802.11(g) or 802.11(n)), the Worldwide Interoperability for Microwave Access (WIMAX®) standard, a short-range wireless communication channel such as BLUETOOTH®, a cellular phone technology (e.g., the Global Standard for Mobile communication (GSM)), a satellite communication link, and/or any other suitable communication means. IEEE is a registered trademark of the Institute of Electrical and Electronics Engineers, Inc., of New York, New York. WIMAX is a registered trademark of WiMax Forum, of Beaverton, Oregon. BLUETOOTH is a registered trademark of Bluetooth SIG, Inc. of Kirkland, Washington.

System 100 may further include a data management system 120 that is coupled to computing device 108 via a network 109. In some embodiments, computing device 108 includes a data management system 120. Data management system 120 may be any device capable of accessing network 109 including, without limitation, a desktop computer, a laptop computer, or other web-based connectable equipment. More specifically, in the exemplary embodiment, data management system 120 includes a database 122 that includes previously acquired data of other subjects. In the exemplary embodiment, database 122 can be fully or partially implemented in a cloud computing environment such that data from the database is received from one or more computers (not shown) within system 100 or remote from system 100. In the exemplary embodiment, the previously acquired data of the other subjects may include, for example, a plurality of measurements of lesion region of other subjects. Database 122 can also include any additional information of each of the subjects that enables system 100 to function as described herein.

Data management system 120 may communicate with computing device 108 using a wired network connection (e.g., Ethernet or an optical fiber), a wireless communication means, such as, but not limited to radio frequency (RF), e.g., FM radio and/or digital audio broadcasting, an Institute of Electrical and Electronics Engineers (IEEE®) 802.11 standard (e.g., 802.11(g) or 802.11(n)), the Worldwide Interoperability for Microwave Access (WIMAX®) standard, a cellular phone technology (e.g., the Global Standard for Mobile communication (GSM)), a satellite communication link, and/or any other suitable communication means. More specifically, in the exemplary embodiment, data management system 120 transmits the data for the subjects to computing device 108. While the data is shown as being stored in database 122 within data management system 120, it should be noted that the data of the subjects may be stored in another system and/or device. For example, computing device 108 may store the data therein.

Figure 2:
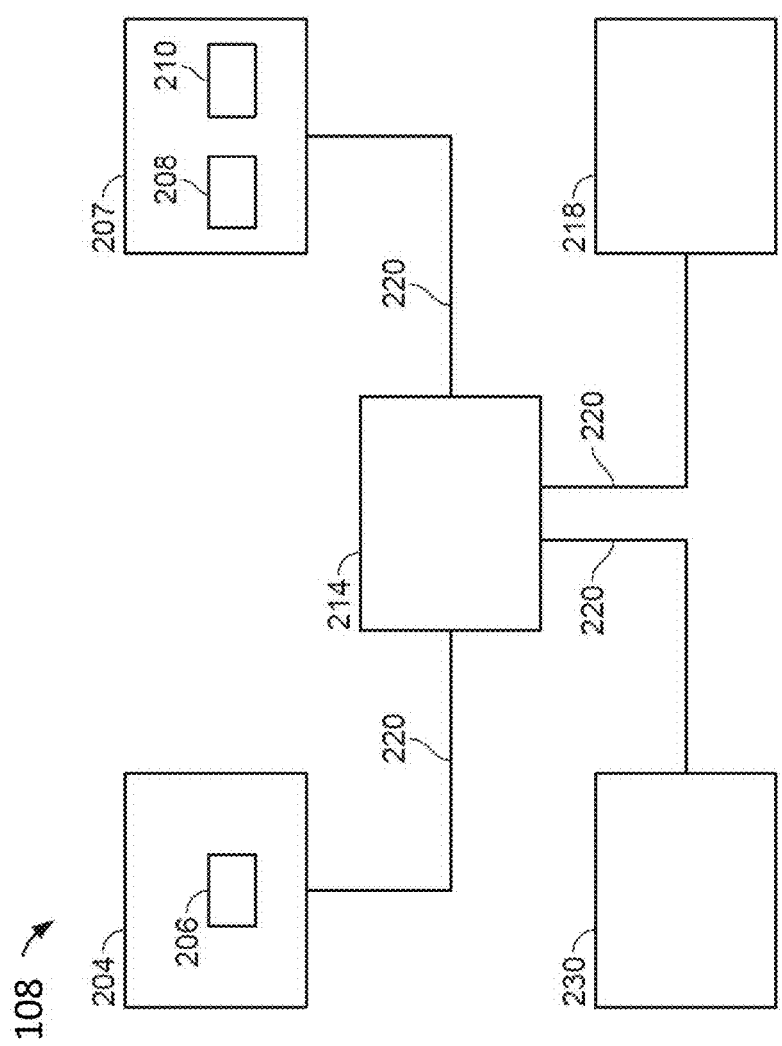
FIG. 2 is a block diagram illustrating a computing device in accordance with an aspect of the disclosure.

FIG. 2 is a block diagram of computing device 108. In the exemplary embodiment, computing device 108 includes a user interface 204 that receives at least one input from a user, such as an operator of imaging device 111 or system 100. User interface 204 may include a keyboard 206 that enables the user to input pertinent information. User interface 204 may also include, for example, a pointing device, a mouse, a stylus, a touch sensitive panel (e.g., a touch pad or a touch screen), a gyroscope, an accelerometer, a position detector, and/or an audio input interface (e.g., including a microphone).

Moreover, in the exemplary embodiment, computing device 108 includes a presentation interface 207 that presents information, such as input events and/or validation results, to the user. Presentation interface 207 may also include a display adapter 208 that is coupled to at least one display device 210. More specifically, in the exemplary embodiment, display device 210 may be a visual display device, such as a cathode ray tube (CRT), a liquid crystal display (LCD), an organic LED (OLED) display, and/or an "electronic ink" display. Alternatively, presentation interface 207 may include an audio output device (e.g., an audio adapter and/or a speaker) and/or a printer.

Computing device 108 also includes a processor 214 and a memory device 218. Processor 214 is coupled to user interface 204, presentation interface 207, and to memory device 218 via a system bus 220. In the exemplary embodiment, processor 214 communicates with the user, such as by prompting the user via presentation interface 207 and/or by receiving user inputs via user interface 204. The term "processor" refers generally to any programmable system including systems and microcontrollers, reduced instruction set circuits (RISC), application specific integrated circuits (ASIC), programmable logic circuits (PLC), and any other circuit or processor capable of executing the functions described herein. The above examples are exemplary only, and thus are not intended to limit in any way the definition and/or meaning of the term "processor."

In the exemplary embodiment, memory device 218 includes one or more devices that enable information, such as executable instructions and/or other data, to be stored and retrieved. Moreover, memory device 218 includes one or more computer readable media, such as, without limitation, dynamic random access memory (DRAM), static random access memory (SRAM), a solid state disk, and/or a hard disk. In the exemplary embodiment, memory device 218 stores, without limitation, application source code, application object code, configuration data, additional input events, application states, assertion statements, validation results, and/or any other type of data. Computing device 108, in the exemplary embodiment, may also include a communication interface 230 that is coupled to processor 214 via system bus 220. Moreover, communication interface 230 is communicatively coupled to imaging device 111, detection subsystem 106, and data management system 120.

In the exemplary embodiment, processor 214 may be programmed by encoding an operation using one or more executable instructions and providing the executable instructions in memory device 218. In the exemplary embodiment, processor 214 is programmed to select a plurality of measurements that are received from imaging device 111 or detection subsystem 106. The plurality of measurements may include, for example, a plurality of voxels of at least one image of the subject, wherein the image may be generated by processor 214 within computing device 108. The image may also be generated by an imaging device (not shown) that may be coupled to computing device 108 and imaging device 111, wherein the imaging device may generate the image based on the data received from imaging device 111 or detection subsystem 106 and then the imaging device may transmit the image to computing device 108 for storage within memory device 218. Alternatively, the plurality of measurements may include any other type measurement of the lesion region that enables system 100 to function as described herein.

Although, in some of the examples provided below, the systems and methods disclosed herein are used on breasts and breast tumors, the systems and methods are not limited to this part of human or animal body or this type of tumor or cancer. Further, method aspects will be in part apparent and in part explicitly discussed in the following description

EXAMPLES

Example 1

System Structure

Figure 3:
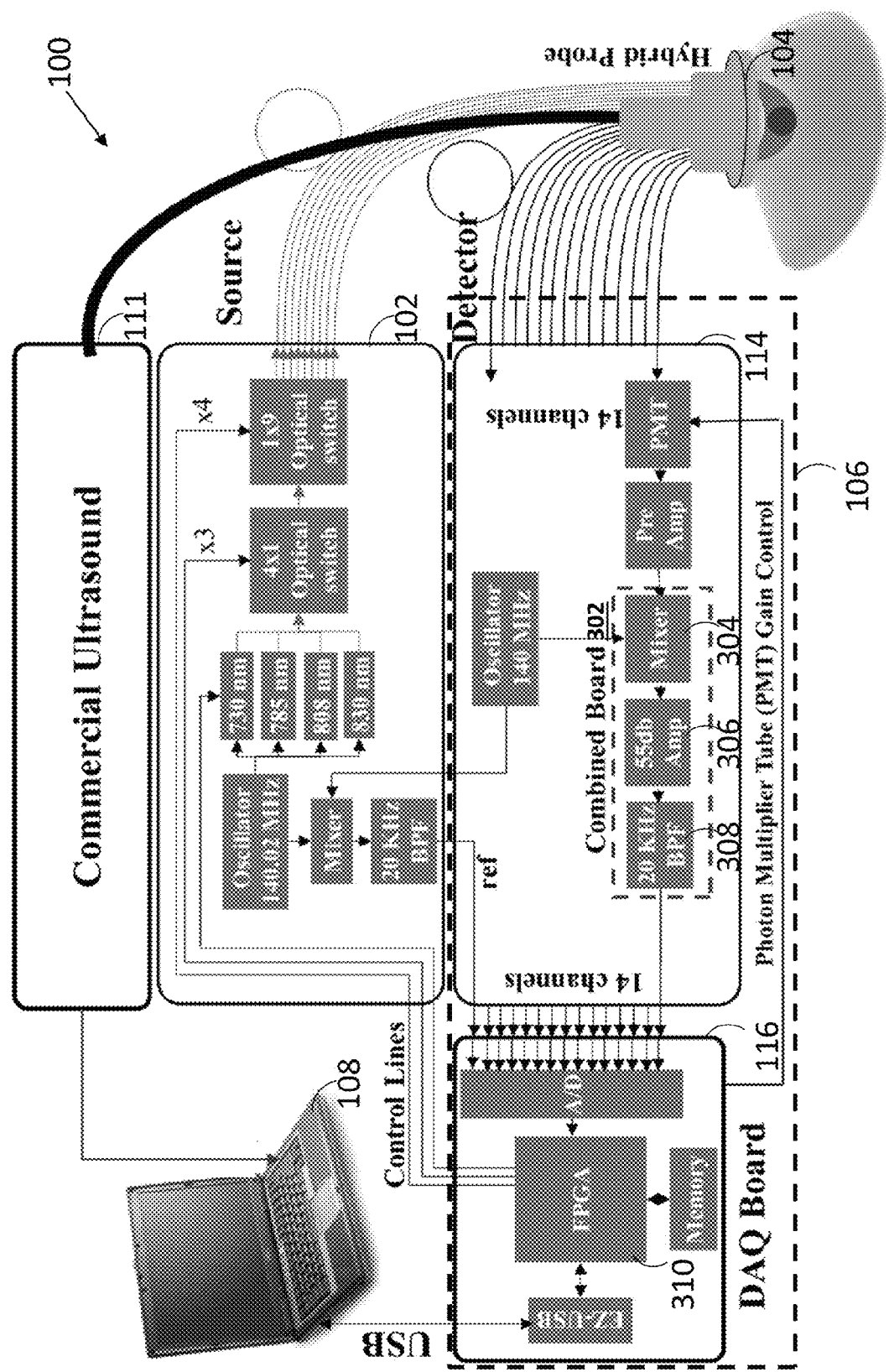
FIG. 3 is a schematic diagram of an exemplary embodiment of the DOT system shown in FIG. 1A.
Figure 4:
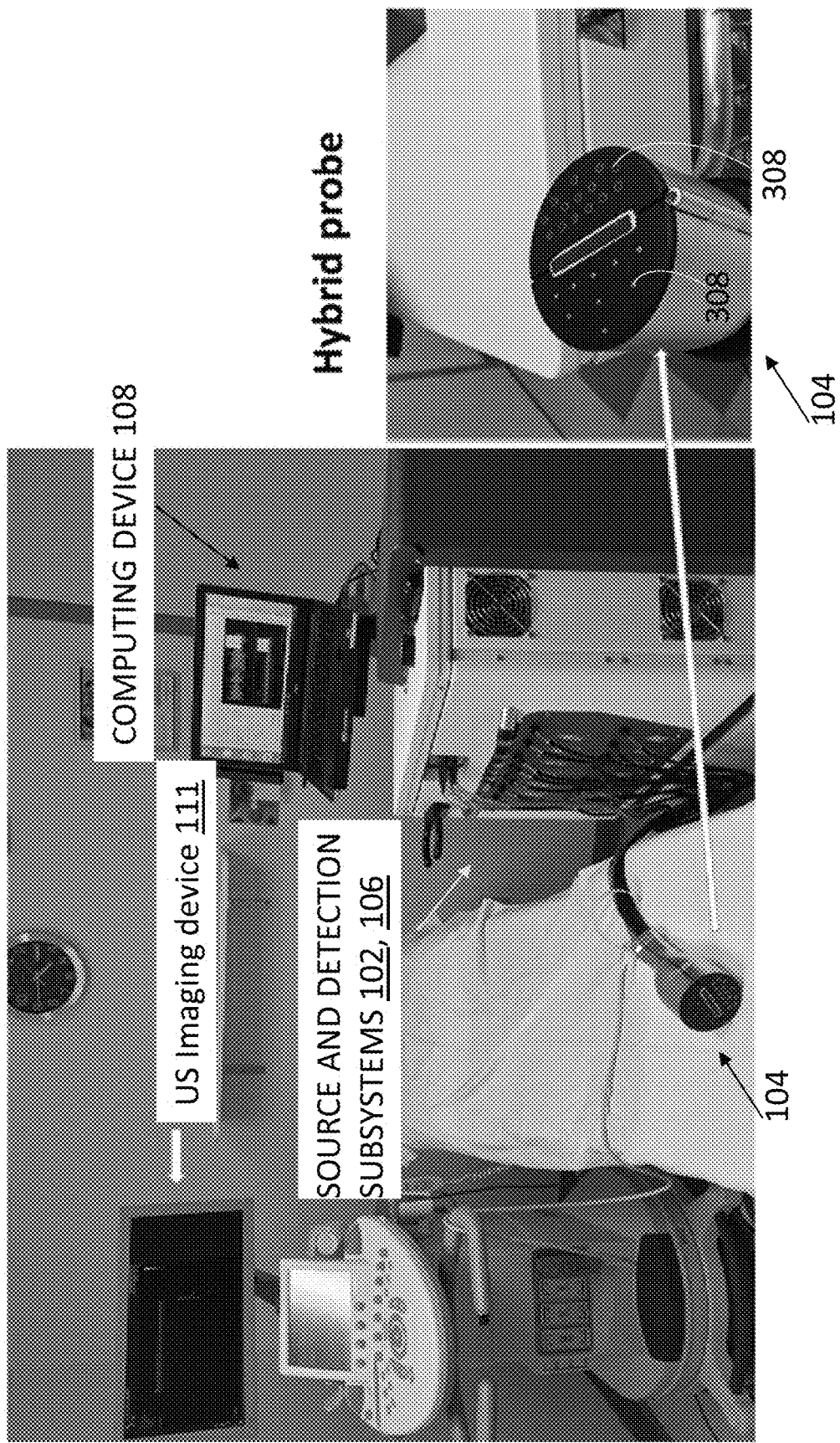
FIG. 4 is a photograph illustrating the DOT system shown in FIG. 3.
Figure 5A:
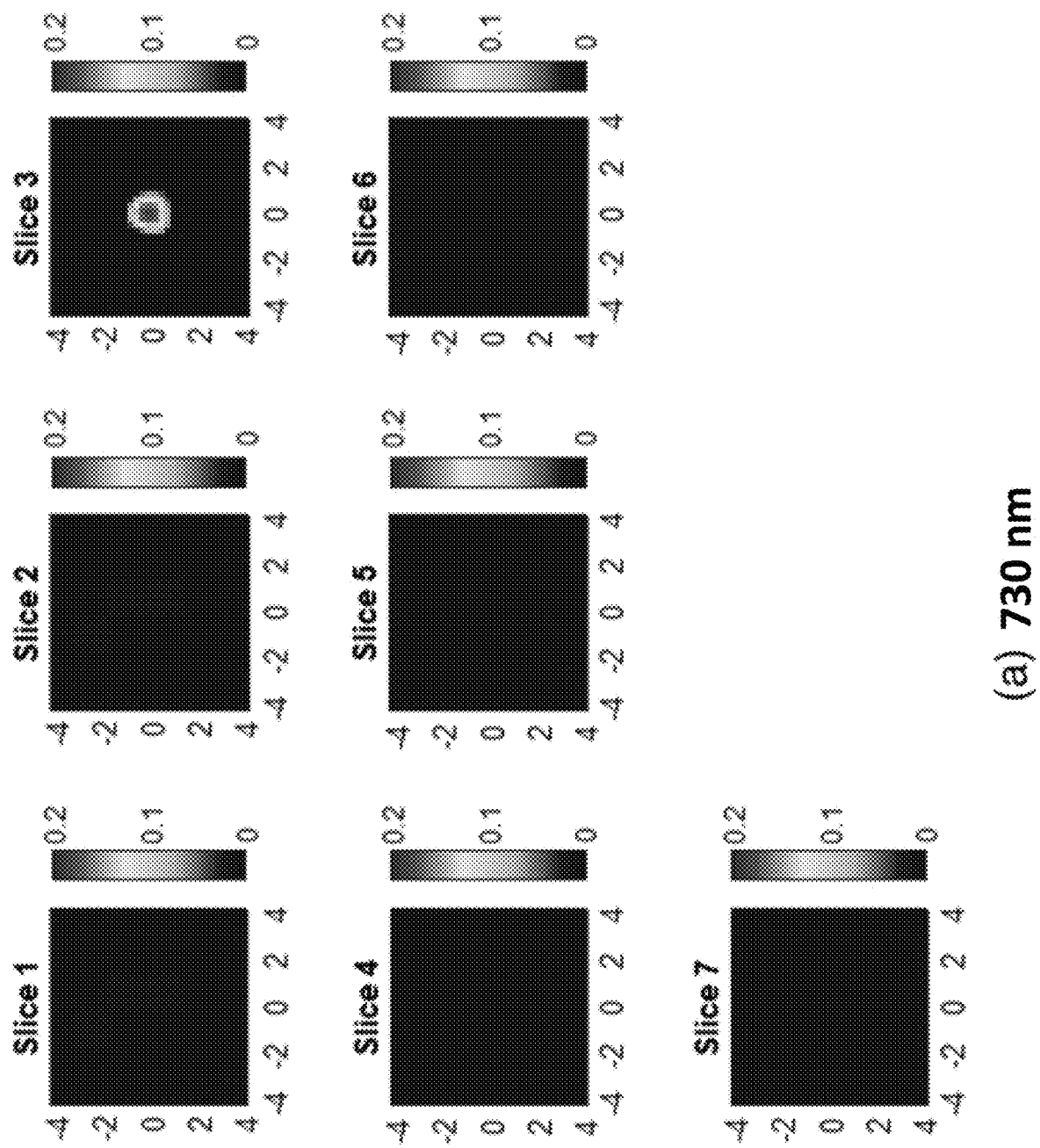
FIG. 5A shows absorption maps of a phantom measured with the DOT system shown in FIG. 3, where the optical waves have a wavelength of 730 nm.
Figure 5B:
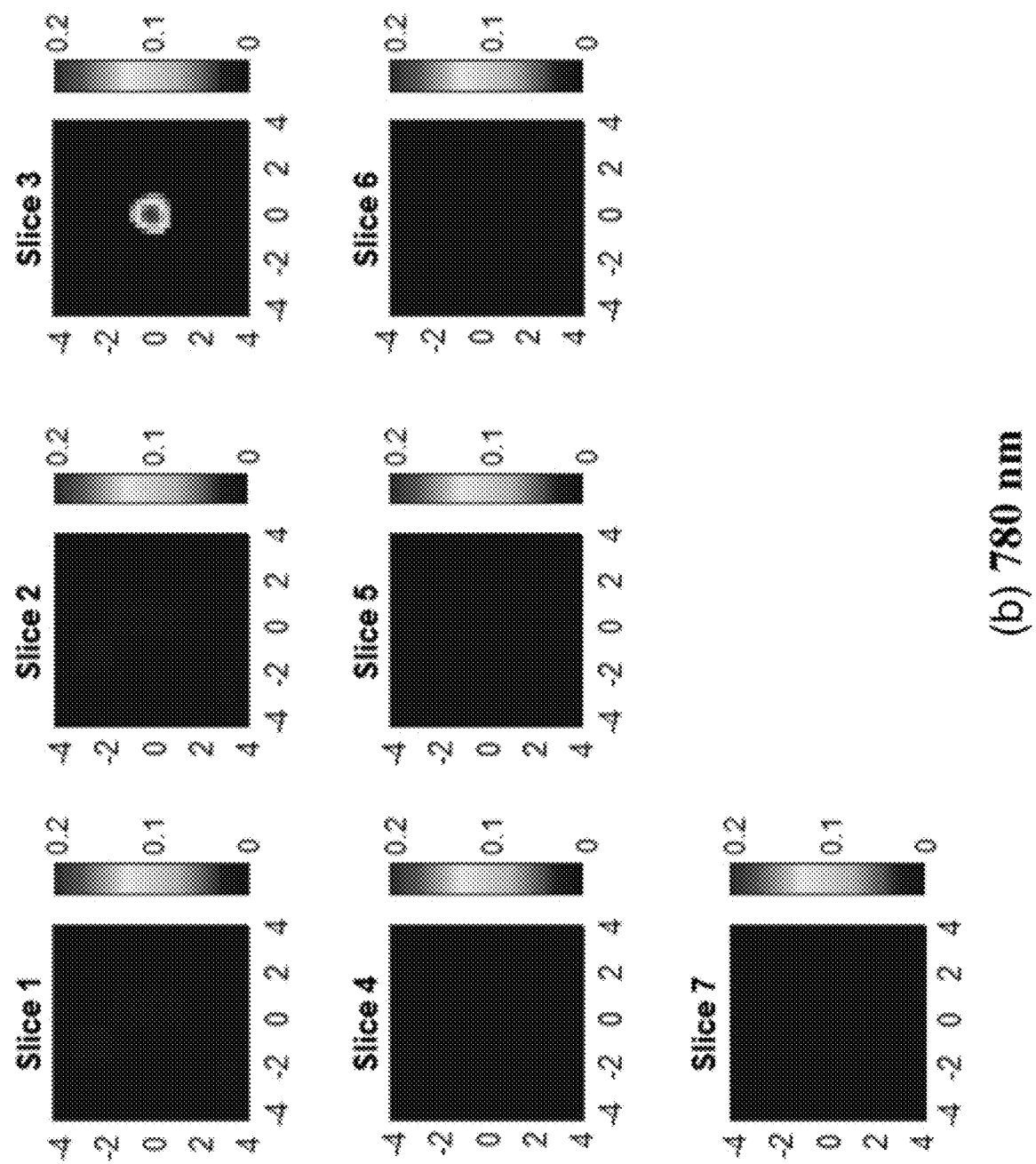
FIG. 5B shows absorption maps of the phantom used for FIG. 5A, where the maps are measured with the DOT system shown in FIG. 3 with the optical waves having a wavelength of 780 nm.
Figure 5D:
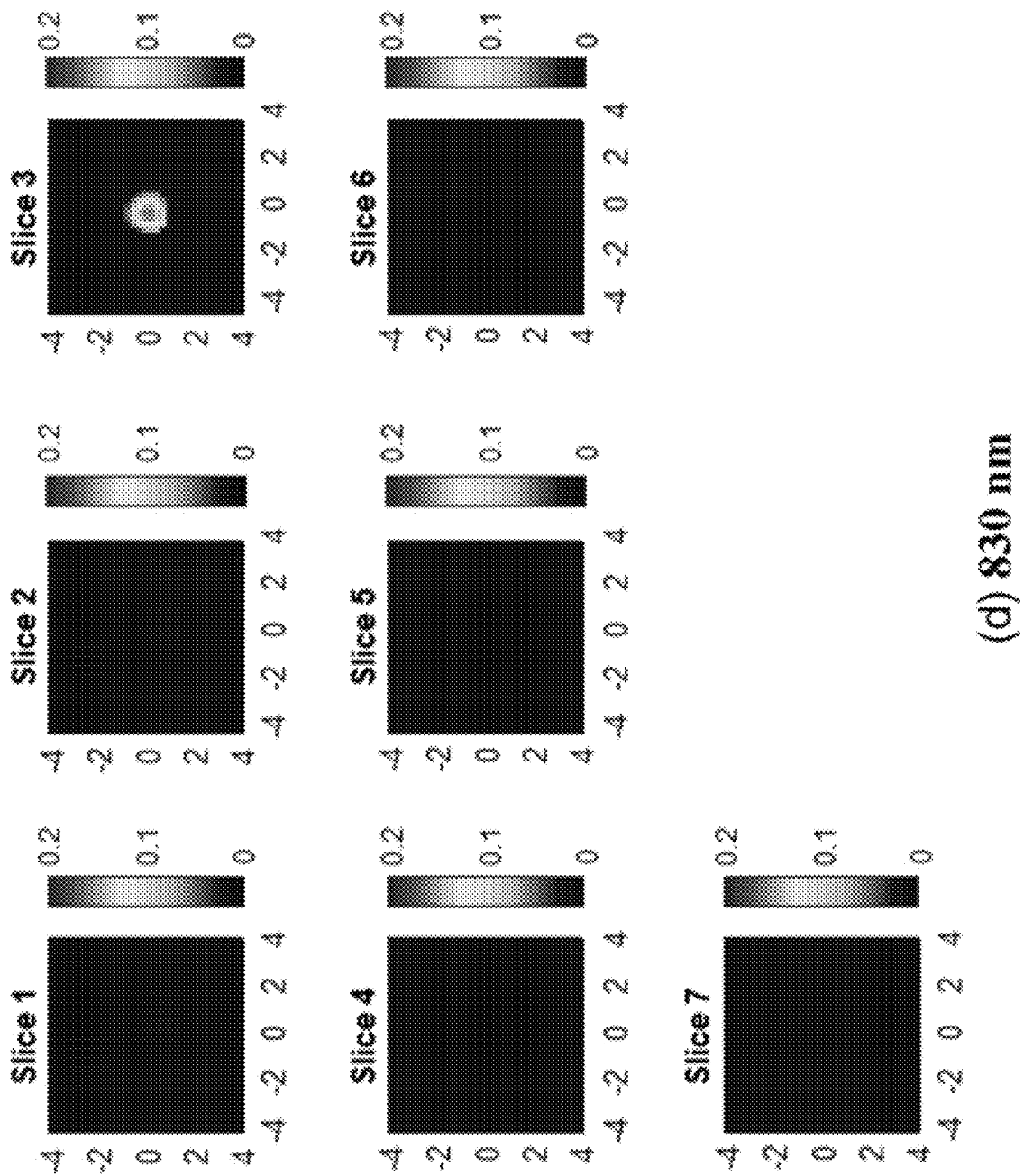
FIG. 5D shows absorption maps of the phantom used for FIG. 5A, where the maps are measured with the DOT system shown in FIG. 3 with the optical waves having a wavelength of 830 nm.

FIG. 3 is a schematic diagram of an exemplary embodiment of compact DOT system 100. System 100 includes source subsystem 102, probe 104, detection subsystem 106, and computing device 108. System 100 may further include an imaging device 111 such as a commercial ultrasound machine, which provides guiding data for system 100. The compact DOT system is designed and constructed to improve the robustness of the earlier prototype DOT systems. Four laser diodes of wavelengths 730, 785, 808, and 830 nm are sequentially switched by 4×1 and 1×9 optical switches to nine source positions on a hand-held probe. The reflected light from each source location is received simultaneously by 14 photomultiplier tube (PMT) detectors. The entire data acquisition lasts about 3 to 4 s. The distance of sources and detectors is between 3.2 and 8.5 cm. The system uses heterodyne detection with the laser diodes modulated at 140.02 MHz and the detected signals are mixed with the 140 MHz reference signal. The output of the mixer at each channel was further amplified and filtered at 20 KHz before being inputted into an analog-to-digital converter (ADC). An instrument case meeting hospital safety standards was custom-designed and manufactured by Nexus LLC. FIG. 4 shows an exemplary clinical set-up of a compact DOT system.

Example 2

Hardware Miniaturization

A miniaturized laser diode driver board, which can accommodate up to six laser diodes, was designed and constructed. A miniaturized detection circuit was designed and built to reduce the total number of unnecessary cables and cost.

Laser Diode Driver and Cooling

The DOT system has two main blocks of source and detection subsystems. In our earlier prototypes, we used four units of Thorlab's DC current driver and four units of temperature-controlled laser diode mounted with an AC modulation port (Thorlab LDM56/M) to drive four laser diodes. These units were bulky and costly. A custom-made laser diode driver board was designed to reduce the bulkiness and cost of these components.

This board can accommodate up to six laser diodes of type A or C with a stable feedback control of DC current for each laser diode. Six built-in bias-tees each with a radio frequency (RF) input provide modulation to each laser diode. The outputs of the laser diodes were multiplexed via two optical switches (Piezosy stem Jena) to nine different positions on the hand-held probe. Four miniature pigtailed laser diodes with a thermal block from OZ Optics (LDPC-T3) were used as sources and the temperature of the diodes were controlled using four units of control modules from Thorlab (TCM1000T TEC). The total size of laser diodes, their driving circuits, and their associated cooling systems have reduced more than 60% as compared with our prototype DOT systems of an early generation.

Miniaturized Detection Board and Data Acquisition Board

A custom-made detection circuit has been designed and built in an effort to miniaturize the detection subsystem. Detection subsystem 106 includes miniaturized detection board 114 and miniaturized DAQ board 116.

In signal detection, because the system has two high frequency oscillators at 140 and 140.02 MHz, respectively, coherent interference at 20 kHz may be generated when signals at the two frequencies interfere with each other in the none-signal paths. To minimize the interference, miniaturized detection board 114 includes a three-layered printed circuit board (PCB) that is designed with a ground layer disposed between the top and bottom layers to reduce the interference. Further, as traces of the top or bottom layer carry high frequency signals at different frequencies, grounded through-holes are placed on both sides of the signal-carrying traces to provide improved signal shielding. This design results in a compact low-noise detection subsystem.

Miniaturized detection board 114 further includes a combined board 302 that incorporates a frequency mixer 304, a second-stage amplifier 306, and a bandpass filter 308, and is formed into one single board. Frequency mixer 304 is configured to mix the detected electrical signals with reference signals to derive mixed signals. Second-stage amplifier 306 is gain adjustable and is designed to provide flexibility in controlling the dynamic range of the detection subsystem. Second-stage amplifier 306 is configured to amplify the mixed signals to derive amplified signals. Bandpass filter 308 is configured to filter the amplified signals to derive electrical signals of a selected frequency. The filtered electrical signals have a high signal to noise ratio (SNR). The selected frequency may be 20 kHz. This new compact detection subsystem provides the same level of coherent noise when compared with each individual component separately shielded and connected. In one example, the overall recorded single channel coherent noise after 80 dB gain is approximately 8 to approximately 10 mV peak-to-peak, and the signal-to-noise ratio at source-detection distance of 8.5 cm for four wavelengths is in the range of 10 to 20 dB measured in an Intralipid solution. Combined board 302 replaces three separate components (a mixer, an amplifier, and a filter) of the detection channel of a prior DOT system. While the three components in the previous system occupied space of 22.5 cm×3.0 cm×5.5 cm in total, this combined board occupies only 10 cm×3 cm×5.5 cm, resulting in approximately 50% size reduction in the largest dimension.

Miniaturized DAQ board 116 is configured to convert the electrical signals outputted by miniaturized detection board 114 to digital signals. Miniaturized DAQ board 116 includes a custom-made field programmable gate array (FPGA) 310 to reduce the DAQ board size and improve its robustness. Miniaturized DAQ board 116 can accommodate up to 16 detection channels with two eight-channel ADC chips. In addition to data acquisition, board 116 is used for controlling the optical switches and PMT gains. Computing device 108, e.g., a laptop PC, is used to communicate with FPGA 310 via a universal serial bus (USB) port.

Example 3

Probe Design

The US transducer is located in the center of the probe to localize the lesion. In order to use PMT detectors in their maximum dynamic range and prevent the saturation when source and detection positions are close, the source-detector distances have been optimized by placing 9 source electrodes 402 on one side of the probe and the 14 detector electrodes 404 on the opposite side of the probe. The inset of FIG. 4 shows a close-up view of hand-held probe 104. A US transducer can be easily inserted into the combined probe holder for coregistered imaging and then be unplugged from probe 104 after the imaging.

Example 4

Software Improvement

Improvements in robustness and user-friendliness of the software for DOT are important steps toward wide use in clinics. A new graphical user interface using C++ with three modules has been developed.

The user interface includes three modules. The first module is DAQ as discussed above. The second module includes automated system calibration. Because individual PMTs have different gains, individual detection electronic channels introduce different phase shifts, and two optical switches have different losses and phase shifts for different source positions, we calibrate gains and phase shifts for all detection channels and source positions. Measurements obtained from an Intralipid solution or a solid phantom of known background absorption and scattering properties are used to form a set of equations. Relative gains and phase delays associated with detector positions and source positions are calculated based on a least squares method. These calibration parameters are applied to amplitude and phase measurements of the contralateral normal breast before calculating bulk optical properties of the tissue in the lesion region. This calibration method is robust and has been included in the automated system calibration.

The third module is imaging reconstruction, which incorporates an outlier removal and data selection before reconstruction to eliminate the need for time-consuming data preprocessing. The method also includes a semi-automated method to select the region of interest (ROI) from coregistered US images and then uses the selected ROI for DOT image reconstruction.

The preprocessing method performs outlier removal, data selection, and data-filtering processes automated for US-guided DOT, which includes a multiple-step process to combine multiple datasets collected from the contralateral normal breast of the patient and form a robust reference dataset. In the multi-step process, datasets from the contralateral normal breast are first stacked together and a statistical method is used to remove outliers from the measurements of each source-detector pair. Then, an iterative reweighted least square method is used to fit the remaining data after the outliers are removed, and any data points having residue more than an empirically selected threshold are further eliminated from the dataset. Next, for each source-and-detector pair, the measurement closest to the center of the remaining data points is selected as the representative of that source-detector pair. The selected measurements for each source-detector pair are combined and formed into a compound and robust reference dataset. Finally, a filtering method is used to remove outliers from the perturbation measurements of the lesion region using a model-based analysis.

Imaging reconstruction is performed after data preprocessing and selection of ROI from coregistered US. The reconstruction uses a two-step image reconstruction method, which has shown to have an improved reconstruction accuracy and speed compared to a previously used conjugate gradient method in a US-guided DOT reconstruction. In the two-step image reconstruction method, a truncated Moore-Penrose pseudoinverse solution is first computed to obtain an initial estimate of the optical properties of a lesion in the lesion region. Next, a penalized least-squares estimator is used to compute the final estimate of the lesion using a Newton or a Conjugate Gradient optimization method. This two-step method shows improvement in accuracy of reconstructed phantom targets of different sizes, optical properties, and placement depths.

Example 5

Phantom Results

Multiple phantom experiments have been designed to evaluate the performance of the system. Phantoms are placed in an Intralipid solution with an absorption coefficient ranging from 0.015 to 0.02 $cm^{-1}$ and a reduced scattering coefficient ranging from 7 to 8 $cm^{-1}$. In a first set of experiments, the sensitivity of the system in differentiating high contrast and low contrast phantoms has been tested. Two sets of solid phantoms with absorption coefficients of 0.11 and 0.23 $cm^{-1}$, respectively, and a reduced scattering coefficient the same as the Intralipid medium measured at 785 nm have been used. Phantoms of three different sizes (having diameters of 1, 2, and 3 cm) placed at different depths include two small 1 cm balls having high and low contrast/absorption coefficients (SHC, SLC), two medium 2 cm high and low contrast balls (MHC, MLC), and two large 3 cm high and low contrast balls (LHC, LLC).

FIGS. 5A-5D show an example of reconstructed images of a SHC ball located at a 1.0 cm depth (measured by the top surface of the phantom from the top surface of the solution) inside the Intralipid solution. The images shown are absorption maps of the phantom when the wavelength of the optical waves is 730 nm (FIG. 5A), 785 nm (FIG. 5B), 808 nm (FIG. 5C), 830 nm (FIG. 5D), respectively. For each set of absorption maps at a different wavelength, seven slices from 0.5 to 3.5 cm depth with 0.5-cm increment have reconstructed. The spatial dimensions of each slice are 9 cm×9 cm. Color bar is the absorption coefficient in the unit of $cm^{-1}$. The reconstruction is performed using the two-step Newton optimization for inversion as described above. The reconstructed maximum absorption coefficients of four wavelengths (730, 785, 808, and 830 nm) are 0.233, 0.238, 0.216, and 0.211 $cm^{-1}$, respectively.

Figure 6:
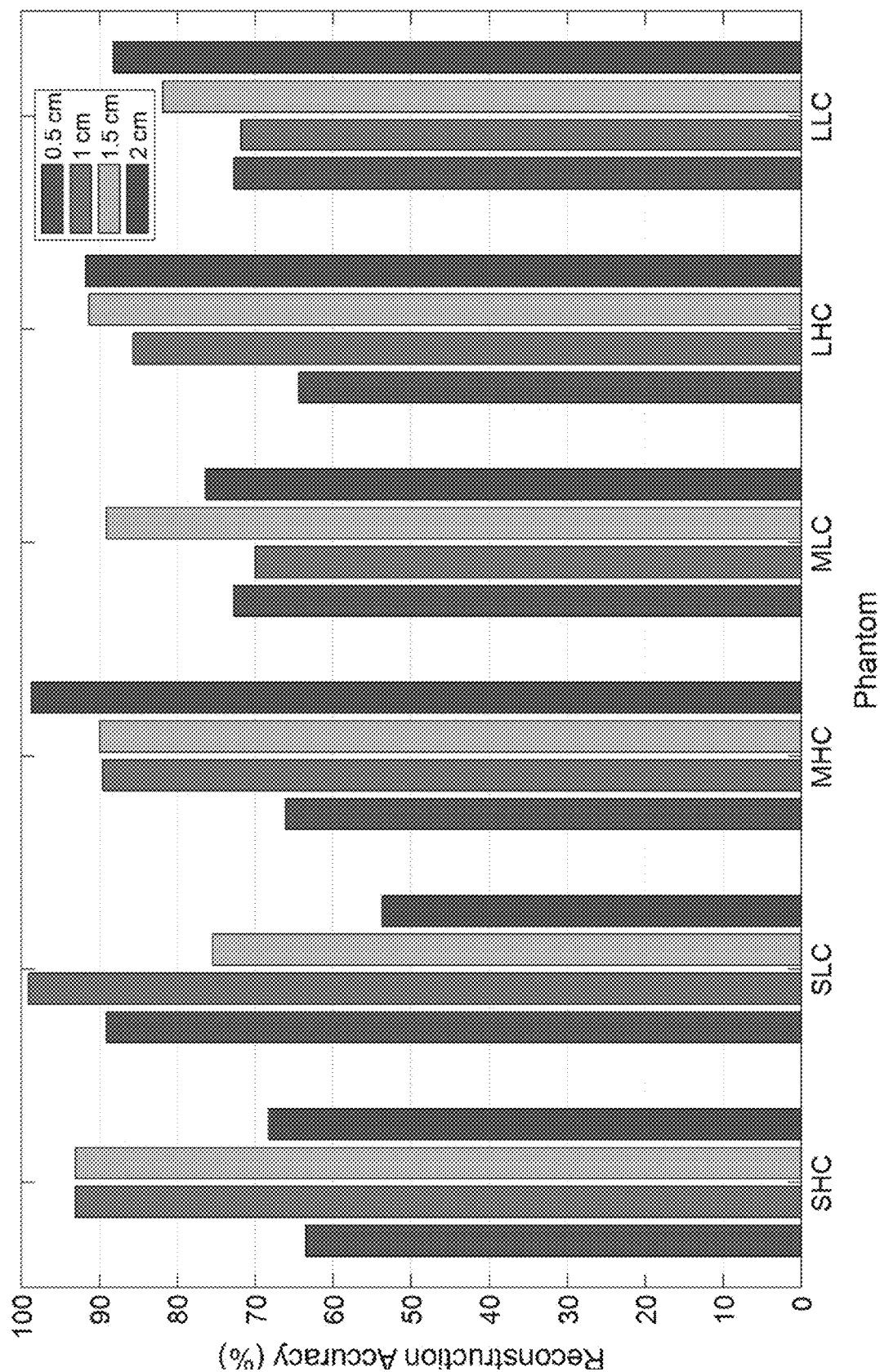
FIG. 6 is a plot showing reconstruction accuracy of phantoms in relation with the placement depths of the phantoms.

FIG. 6 shows the reconstruction accuracy (%) of the maximum reconstructed absorption coefficients of six solid phantoms having high contrast or low contrast and located at different depths. The maximum coefficients used in FIG. 6 are averages of the four maximum absorption coefficients measured at the four wavelengths. The top depths of the phantoms (measured from the top surface of the phantom from the top surface of the solution) are shown in the figure. For high-contrast phantoms, our DOT system is accurate in the depth range of 1 to 2 cm for 1-cm diameter phantom (89.4%, SHC), and 1 to 2.5 cm for 2 cm (97.2%) and 3-cm (87.6%) diameter phantoms (MHC, LHC). For low contrast phantoms, DOT system is accurate in the depth range of 0.5 to 2 cm for 1-cm diameter phantom (73%, SLC), and 0.5 to 2.5 cm for 2 cm (69.5%) and 3 cm (72.1%) diameter phantoms (MLC, LLC). For high contrast phantoms located close to the surface, such as less than 1 cm, the accuracy of reconstruction is reduced (64.4%) due to lack of central sources in the combined probe. This lack of a single center source in the probe to illuminate the lesion underneath is because a US array occupies the center of the combined probe. The source-and-detector pairs with "banana" patterns in probing the central region have a minimum source-detector distance of 3 cm, which results in reduced sensitivity in shallower depths, such as less than 1 cm.

Figure 7:
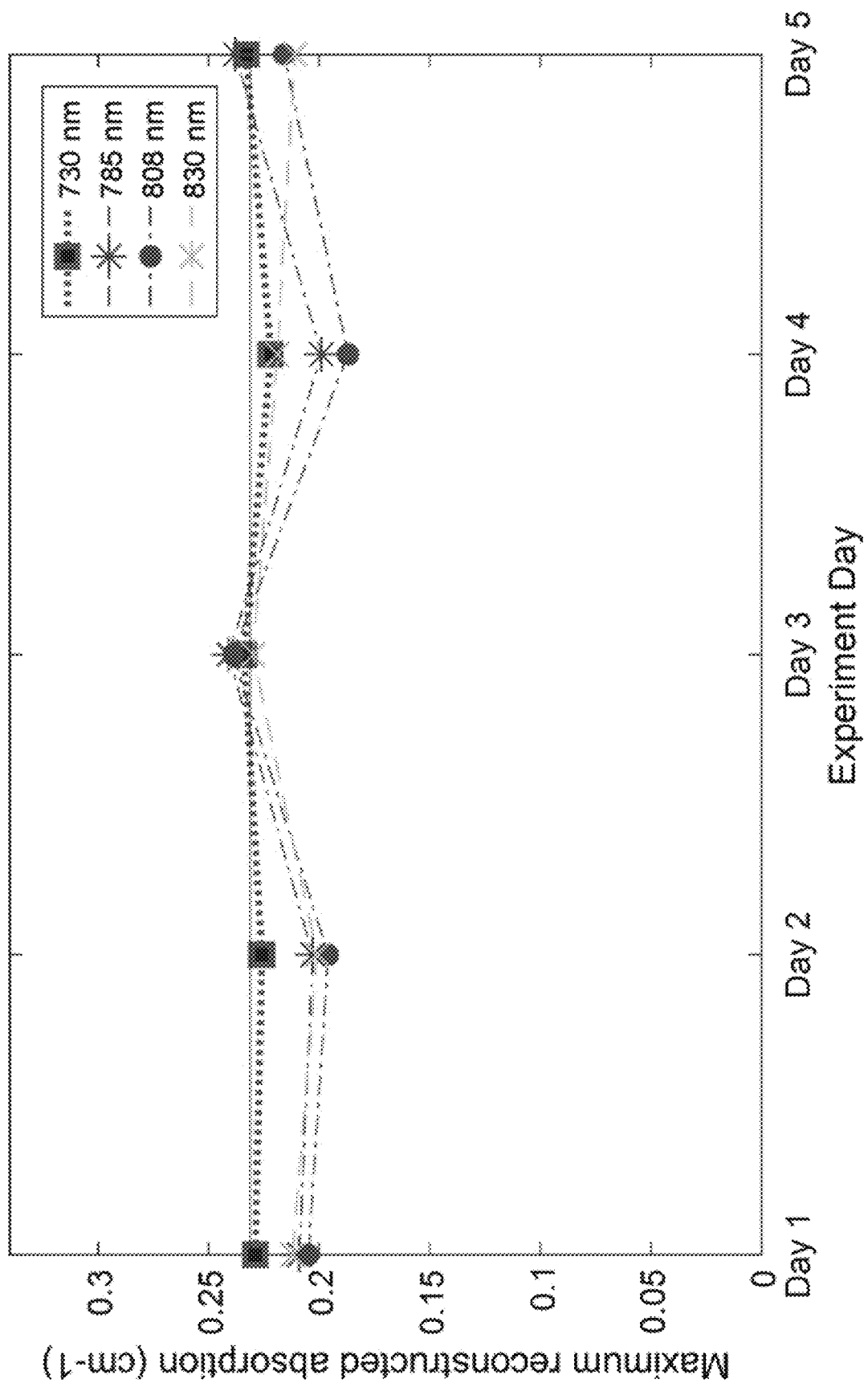
FIG. 7 is a plot showing the measured maximum reconstructed absorption coefficient in relation with measurement dates.

To further evaluate the stability of the system over time, a series of experiments of phantoms are conducted on different days. Exemplary stability results are presented in FIG. 7, which includes maximum reconstructed absorption coefficients of a 1 cm diameter high-contrast target measured at four optical wavelengths (730 nm, 785 nm, 808 nm, and 830 nm) on different days. The black line represents the calibrated (true) absorption of the phantom. The target is located at 1.0 cm depth (top surface of the phantom). The experiments have been repeated for 5 days with one measurement performed per day. The average variation over the five days is 5.4%, which is negligible, compared to the measurement errors of locating the targets inside the Intralipid solution at the desired depths.

Figure 8B:
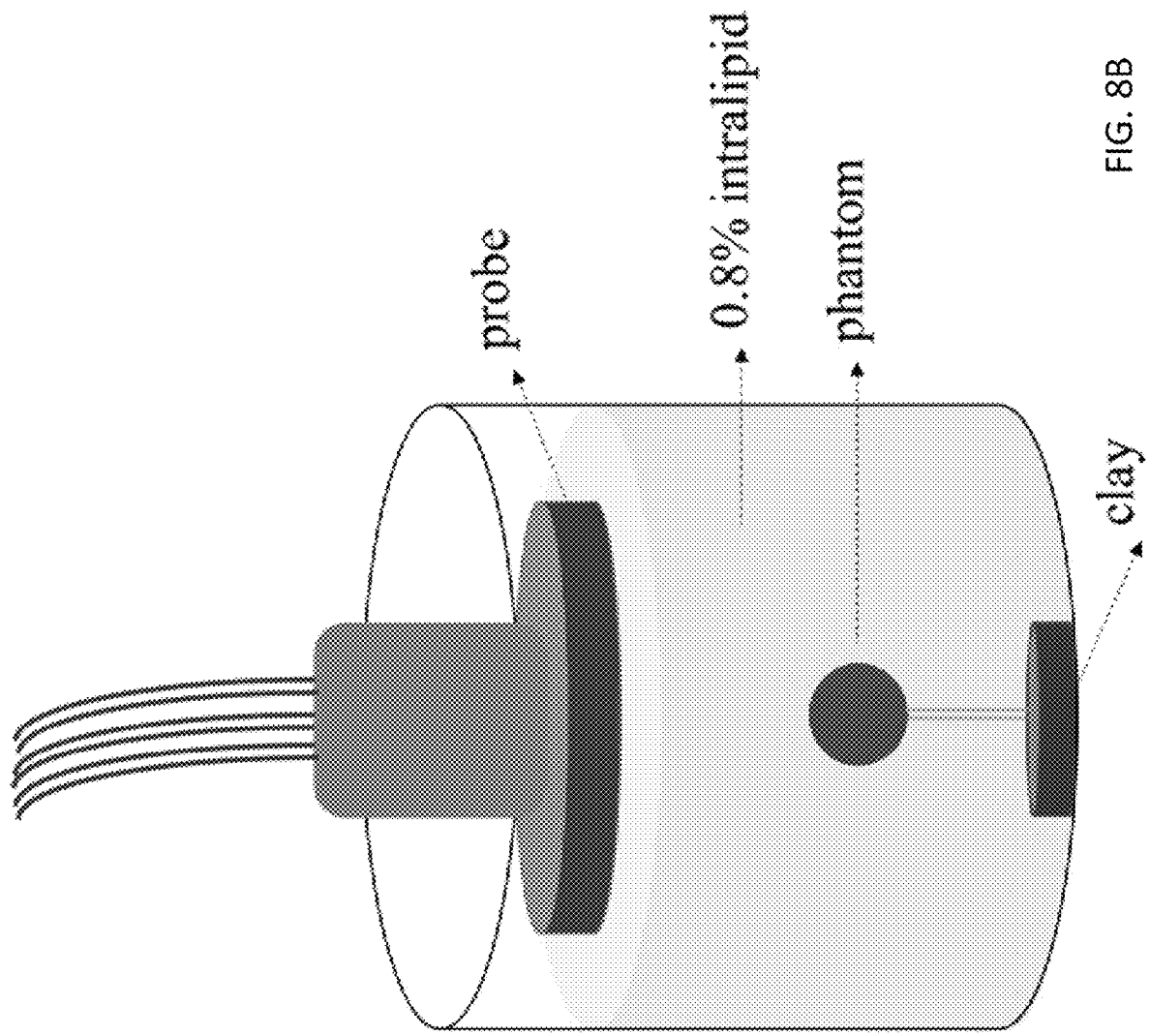
FIG. 8B shows an experimental setup using the phantom shown in FIG. 8A.
Figure 8A:
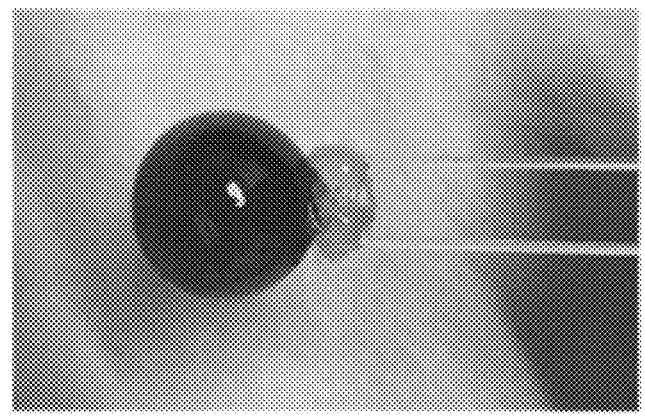
FIG. 8A is an image of a hemoglobin phantom.

The sensitivity of the system to oxygenated and deoxygenated hemoglobin is also evaluated. A hollow glass bulb filled with oxygenated and deoxygenated hemoglobin is used as a blood phantom. Hemoglobin solution was purchased from Instrumentation Laboratory (multi-4, level 2, Instrumentation Laboratory, Mass.) as an oxy-Hb sample. The multi-4, level 2 product specification provided by Instrumentation Laboratory is the total hemoglobin of 139 g/L, with the $HbO_2$ percentage of approximately 97%. The deoxygenated hemoglobin (Hb) solution is prepared by adding sodium dithionite ($Na_2S_2O_4$) solution into diluted oxygenated hemoglobin ($HbO_2$). For example, 0.05 g of sodium dithionite is dissolved in 0.5 mL, phosphate-buffered saline solution (with 10 μL mixed solution corresponding to 1 mg sodium dithionite) with pH of 7.4. We then add the sodium dithionite solution into 3.5 mL of $HbO_2$ solution to prepare an Hb solution. Solution preparation and mixing are carried out on top of dry ice to keep the temperature at around 0° C., which slows down the speed of deoxygenated Hb reacting with $O_2$. After sealing of the glass ball, we incubate it at around 37° C. for 6 min. for the sodium dithionite to be effective. We calibrate the deoxygenating process with a standard UV-Vis spectrometer (Varian Cary®, Agilent). For each ball and Hb solution, we finish our DOT measurements in less than 10 min. FIGS. 8A and 8B presents the experimental setup for the hemoglobin phantom experiments. FIG. 8A shows a glass ball (0.9 cm radius) phantom filled with $HbO_2$ solution and connected to holding fibers. FIG. 8B is a sketch of the experimental setup.

Figure 9:
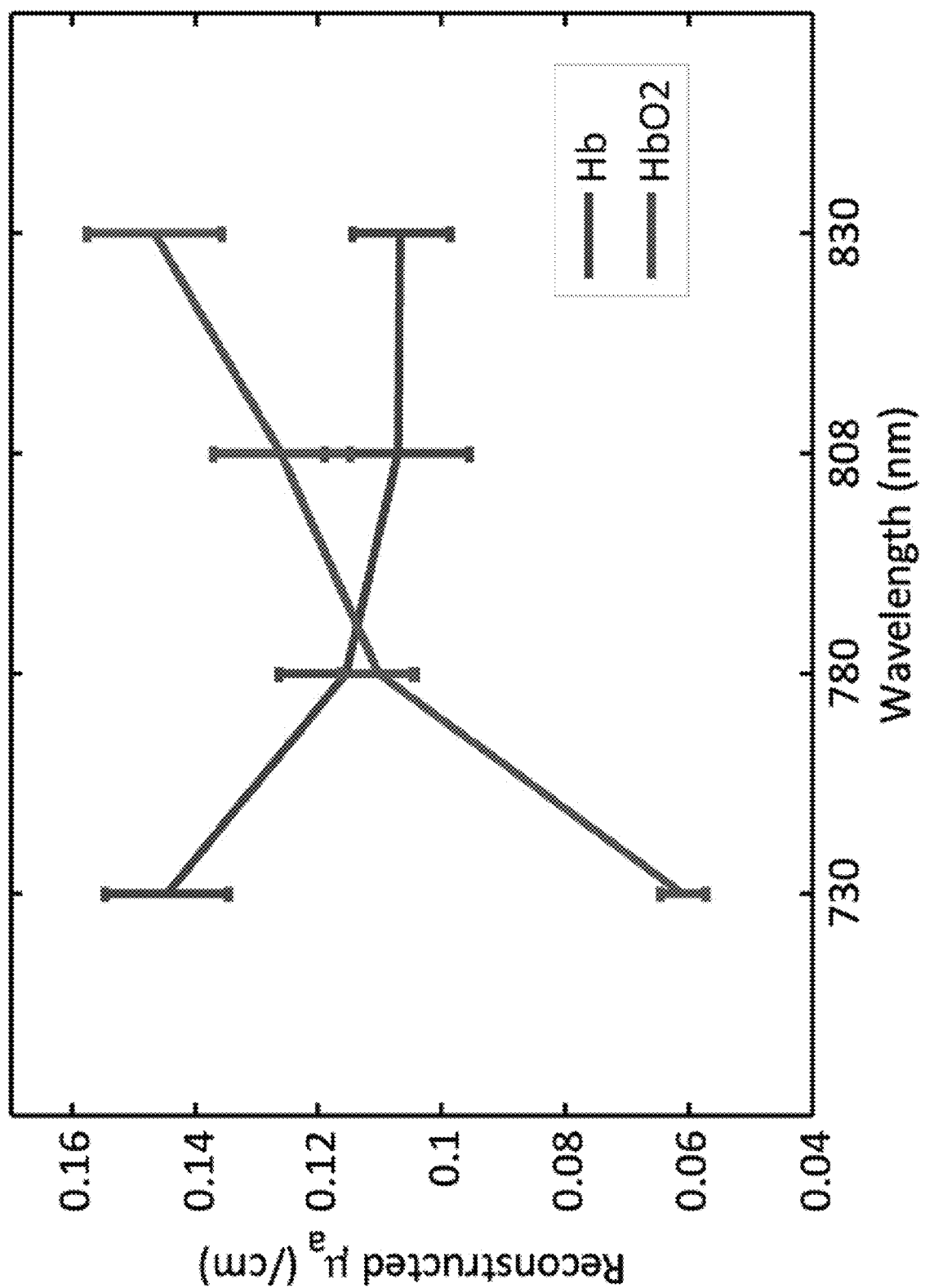
FIG. 9 is a plot showing a spectrum of reconstructed absorption coefficients measured with the DOT system shown in FIG. 3.

Images are reconstructed from measured data and the maximum reconstructed absorption coefficients $\mu_a$ were compared with calibrated values using a spectrometer. We used the maximum reconstructed $\mu_a$ to compute $SO_2$. We analyze the DOT-measured $SO_2$ of the hemoglobin target at different calibrated $SO_2$ values (approximately 5% to approximately 10% and approximately 97%). FIG. 9 shows oxygenated and deoxygenated hemoglobin spectrum of reconstructed absorption coefficients using the DOT system, which is consistent with the trends of the oxygenated and deoxygenated hemoglobin in literature data.

Figure 10:
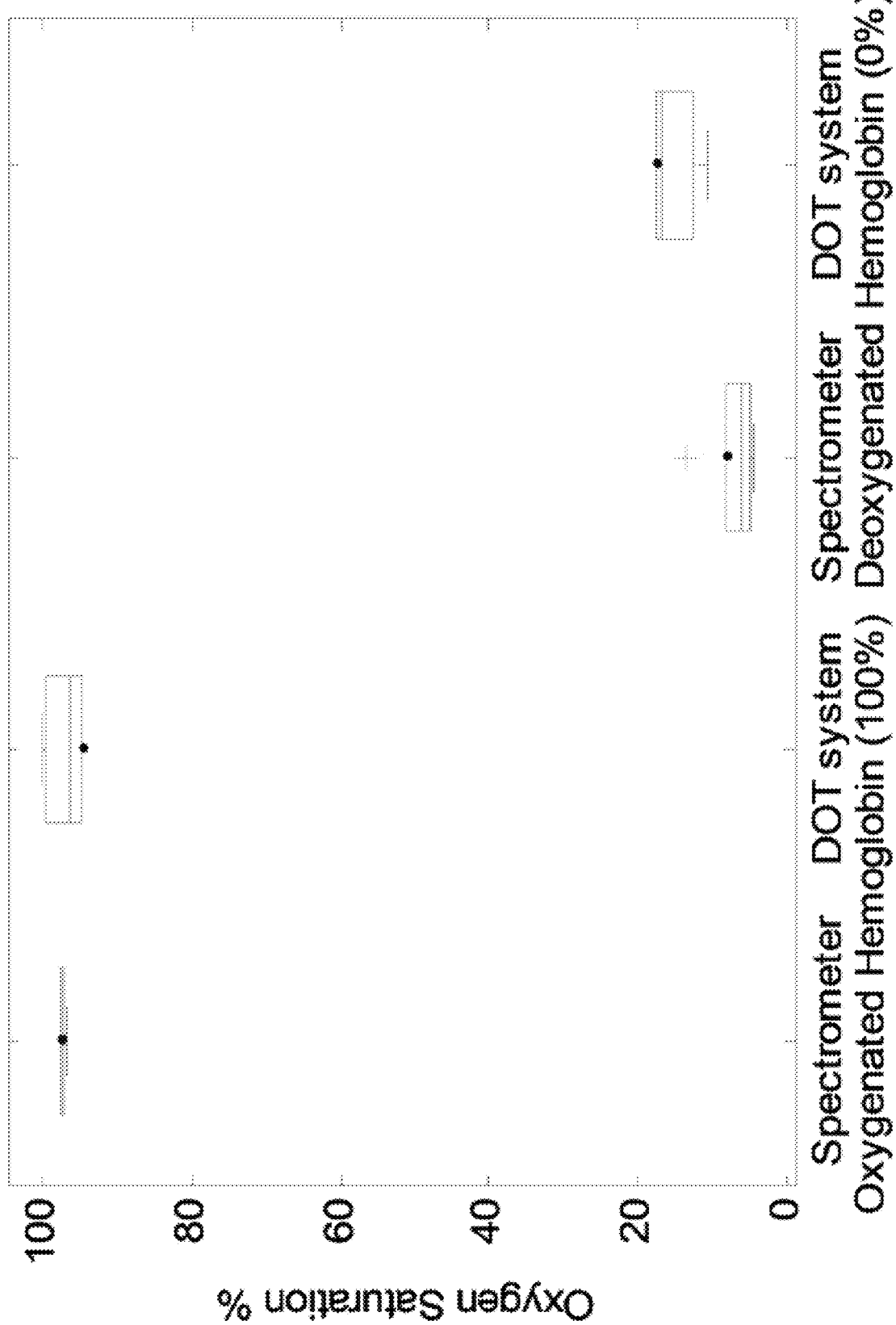
FIG. 10 is a plot comparing measurements of oxyHb and deoxyHb by the DOT system shown in FIG. 3 and by a spectrometer.
Figure 11A:
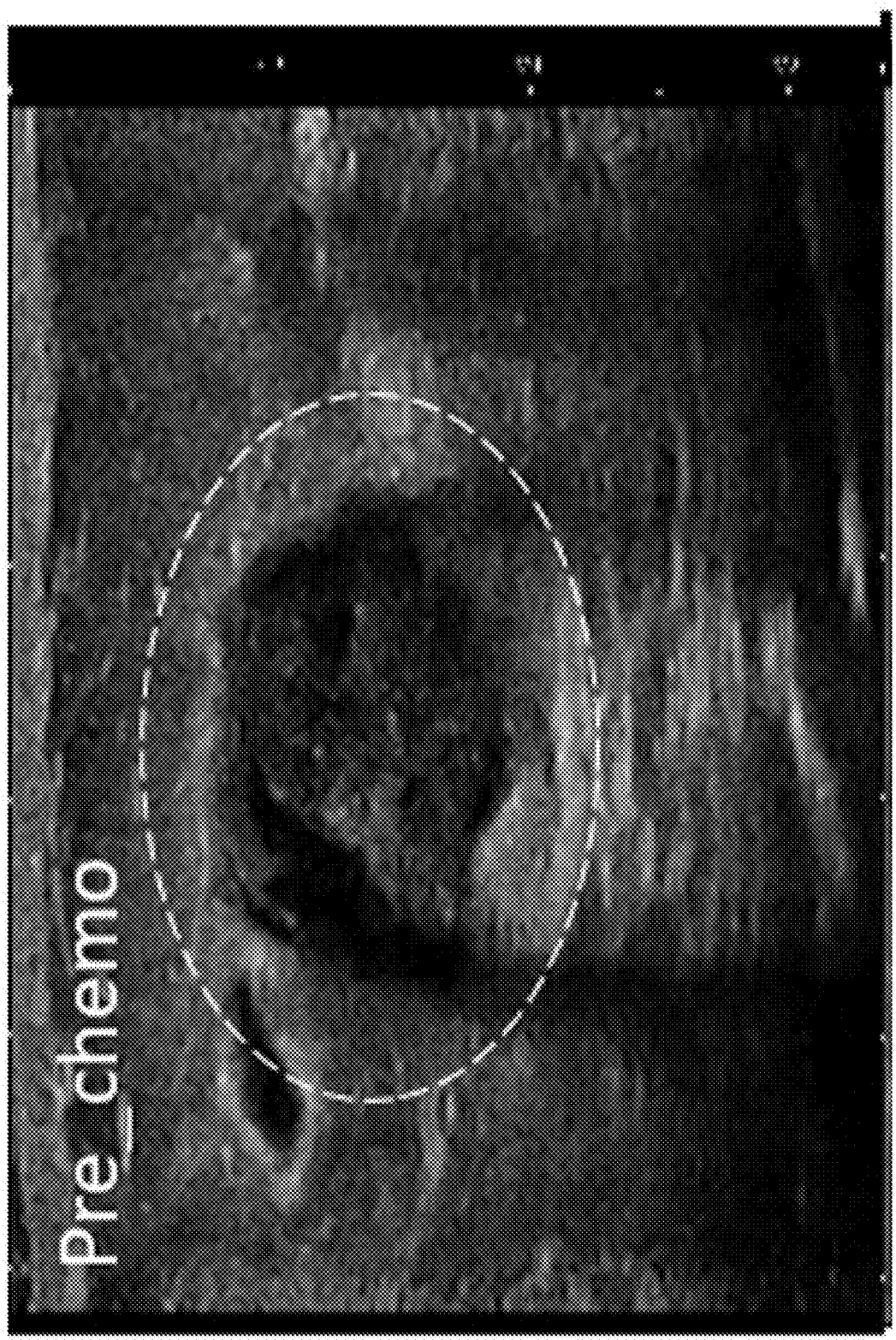
FIG. 11A is an ultrasound (US) breast image of a subject obtained before a treatment.
Figure 11B:
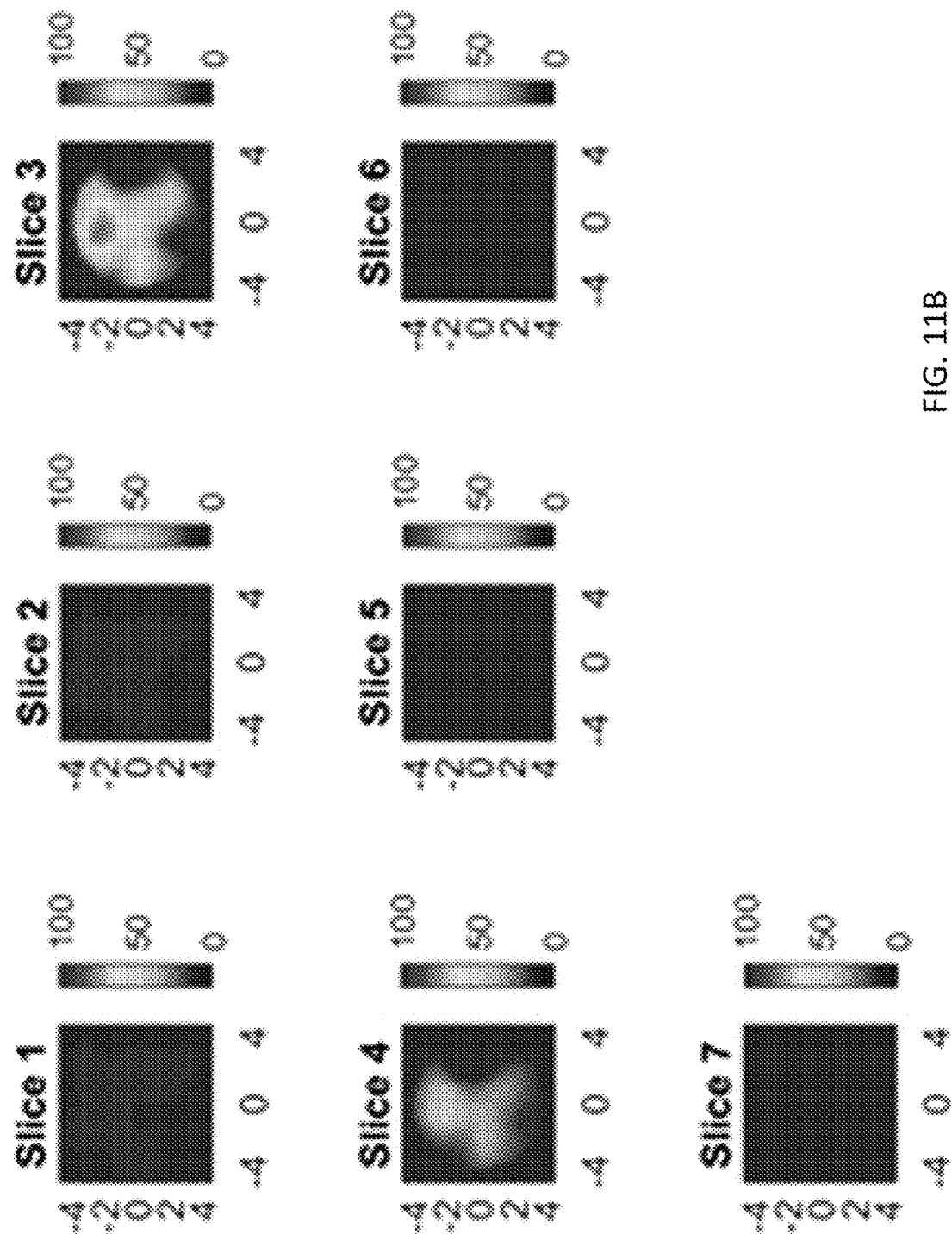
FIG. 11B are total hemoglobin concentration (tHb) maps of the region marked in FIG. 11A.
Figure 12A:
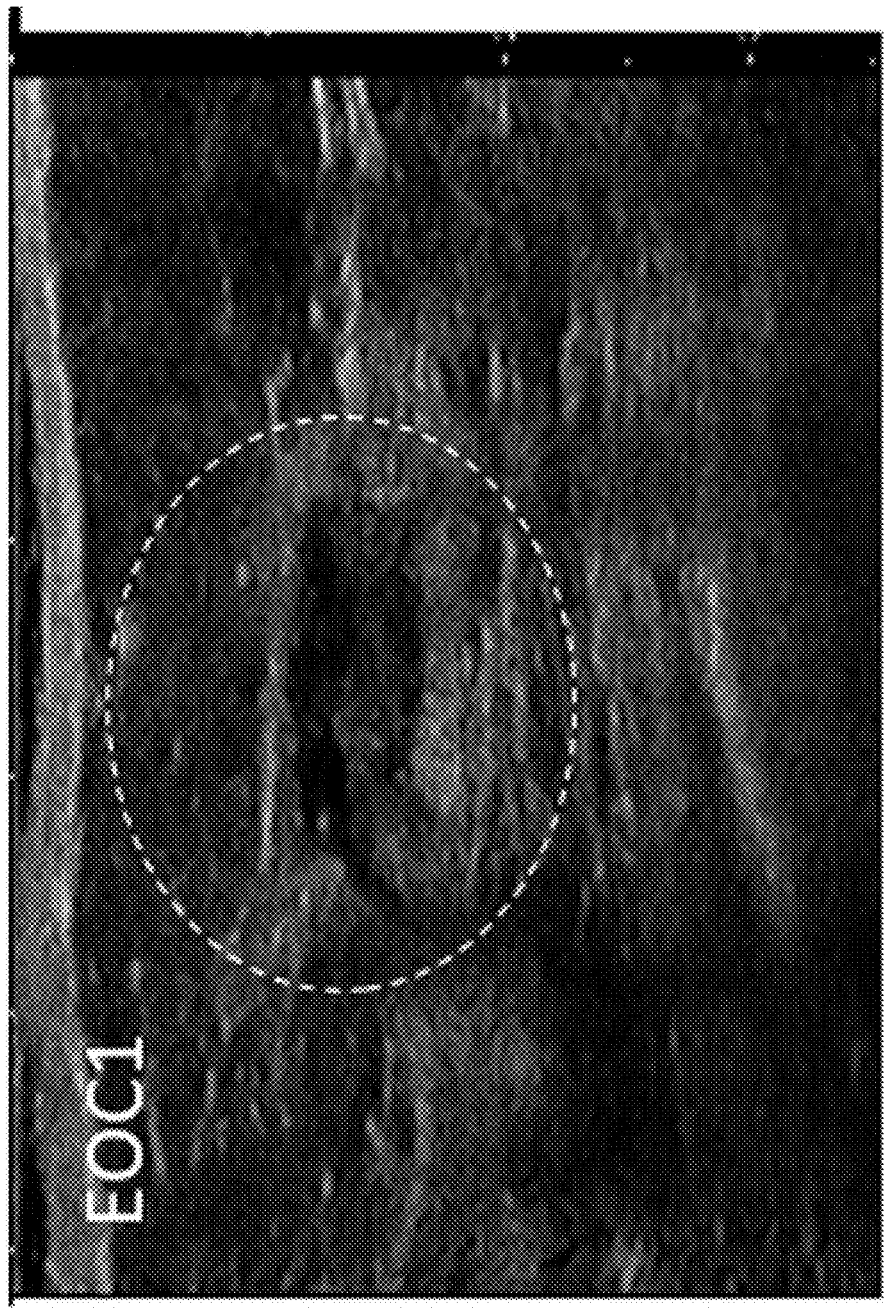
FIG. 12A is an US image of the same breast region as in FIG. 11A, where the image was obtained at the end of cycle 1 of the treatment.
Figure 12B:
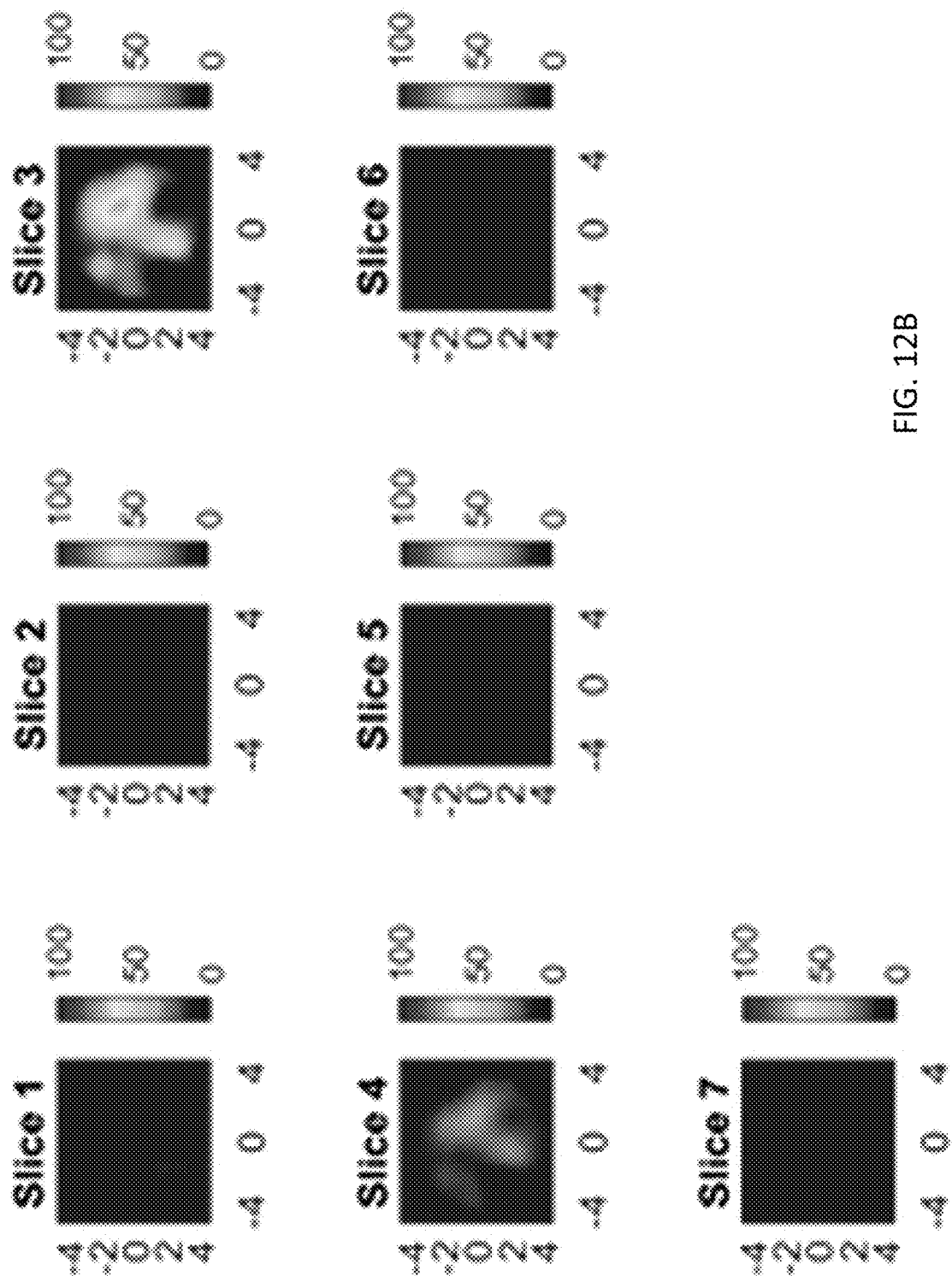
FIG. 12B are tHb maps of the region marked in FIG. 12A.
Figure 13A:
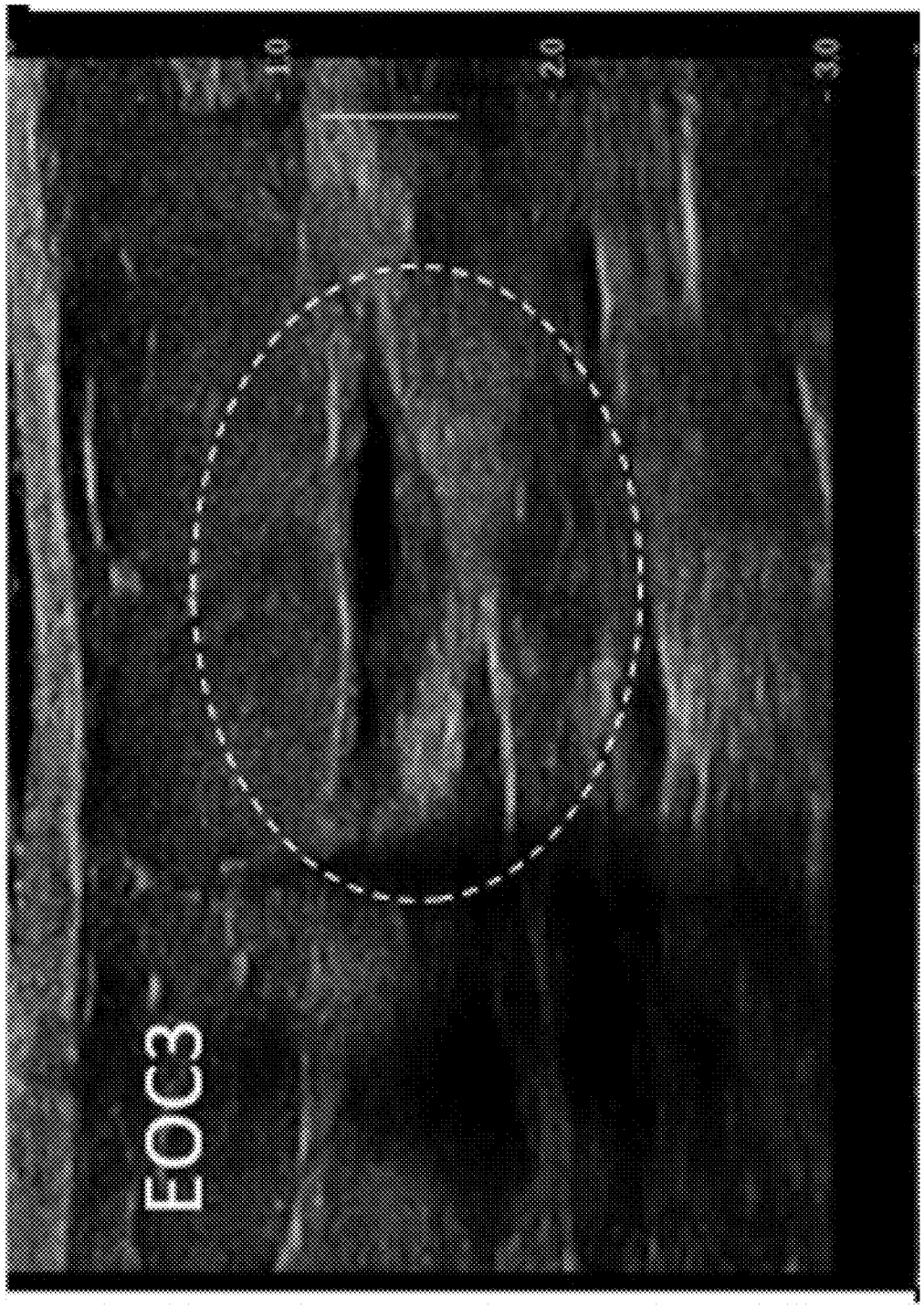
FIG. 13A is an US image of the same breast region as in in FIG. 11A, where the image was obtained at the end of cycle 3 of the treatment.
Figure 13B:
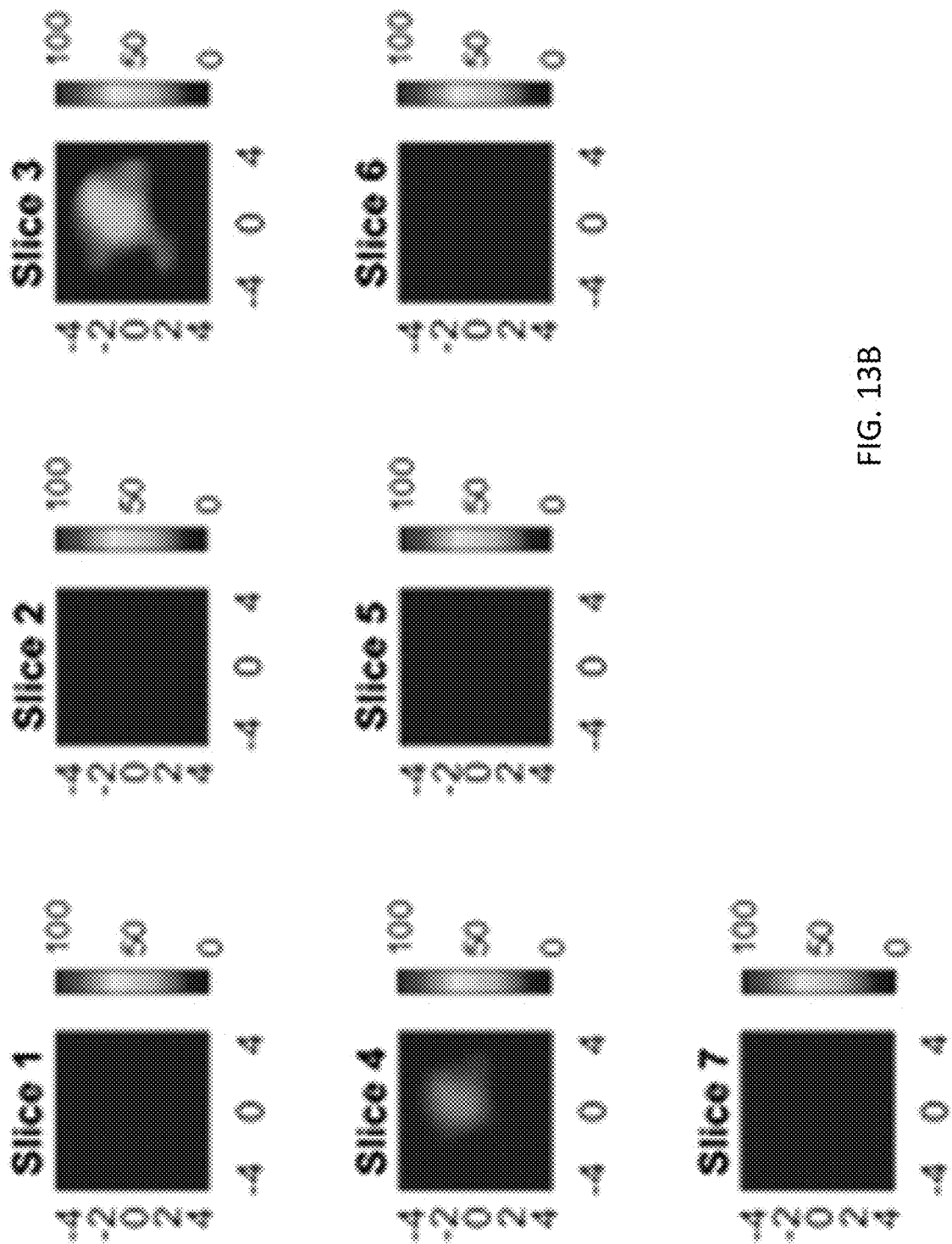
FIG. 13B are tHb maps of the region marked in FIG. 13A.
Figure 14A:
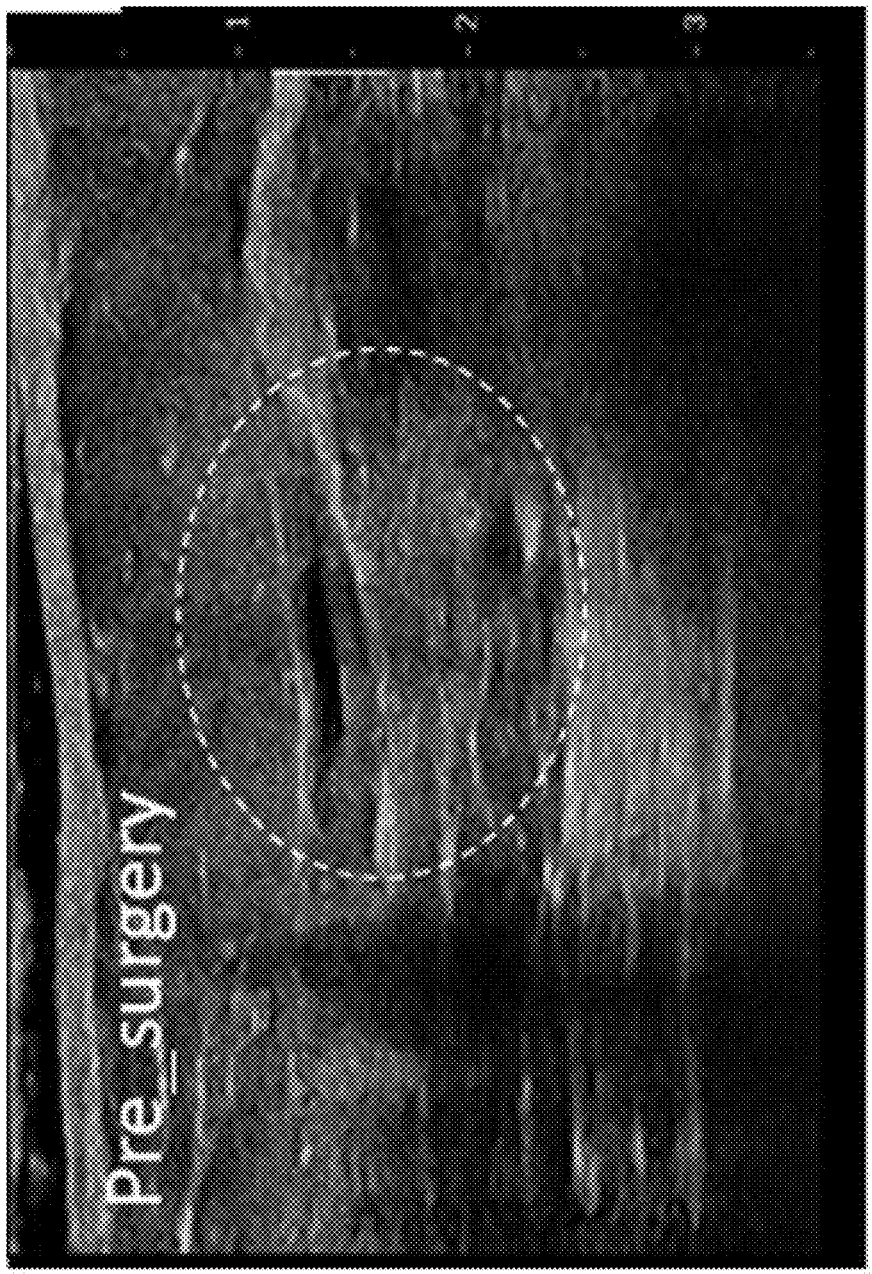
FIG. 14A is an US image of the same breast region as in FIG. 11A, where the image was obtained before surgery.
Figure 14B:
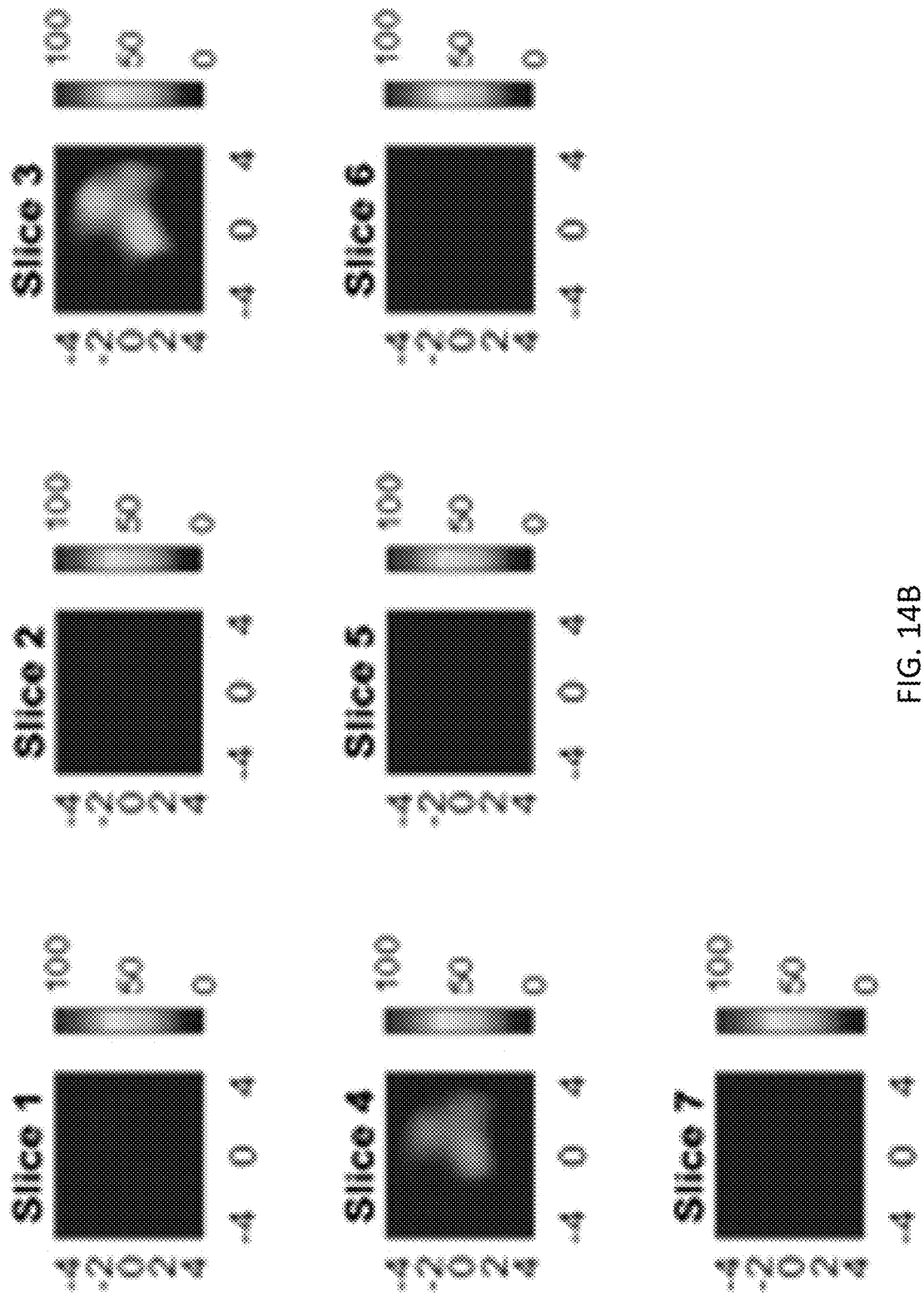
FIG. 14B are tHb maps of the region marked in FIG. 14A.

The results of the DOT system with four wavelengths are also comparable to the data obtained from the spectrometer (FIG. 10). To evaluate the system's sensitivity to oxygenated and deoxygenated hemoglobin over time, five samples of oxygenated hemoglobin and five samples of deoxygenated hemoglobin are prepared. Each day, one oxygenated sample and one deoxygenated sample are prepared and measured by both spectrometer and DOT system. FIG. 10 shows the comparison of the five oxygenated and deoxygenated samples of calibrated values by a spectrometer and calculated values by the DOT system. It can be seen that the DOT measurements follow the spectrometer results closely.

Example 6

Clinical Results

The system is used in patients undergoing neoadjuvant treatment. The study protocol was approved by the institutional review board and was HIPPA compliant. Written informed consent was obtained from patients. The final pathologic responses are evaluated by the Miller-Payne (MP) system. In the MP system, patient pathologic responses are divided into five grades based on comparison of tumor cellularity between pre-neoadjuvant core biopsy and definitive surgical specimen. MP1 and 2 indicate no change or some minor loss of tumor cells (up to 30%) but with overall cellularity still high. This is a partial pathologic response (pPR). MP 3 indicates an estimated 30% to 90% reduction in tumor cells (also a pPR). MP 4 indicates a marked disappearance of tumor cells (>90%), with only small clusters or widely dispersed individual cells remaining (almost a pathologic complete response (pCR)). MP 5 indicates no malignant cells are identifiable in sections from the tumor bed (pCR). Grade 5 may show necrosis, granulation tissue, histiocytes, vascular fibroelastotic stroma, and macrophages. Residual ductal carcinoma in situ (DCIS) is considered as MP grade 5.

An example of US-guided DOT generated total hemoglobin maps acquired throughout neoadjuvant treatment in a 51-year-old woman with a pCR is shown in FIGS. 11A-14B. The patient presented with a high grade (Nottingham histologic score 9/9) triple-receptor-negative (TN), (i.e., ER-, PR-, Her2 Neu-) invasive ductal carcinoma and was treated with carboplatin and docetaxel every three weeks for six cycles. US and US-guided DOT was obtained prior to treatment, at the completion of cycles 1, 2 (not shown), and 3, and before surgery. FIGS. 11A, 12A, 13A, and 14A show the US images at time points of pretreat, after cycle 1, after cycle 3, and presurgery. FIGS. 11B, 12B, 13B, and 14B show the corresponding tHb maps of the regions marked in FIGS. 11A, 12A, 13A, and 14A with a dashed oval, respectively. The tHb maps are acquired with the DOT systems disclosed herein. Each set of maps includes seven subimages marked as slices 1 to 7 and each subimage shows spatial x and y distribution (9 cm×9 cm) of tHb concentration at depths ranging from 0.5 to 3.0 cm depth range from the skin surface. The spacing between the subimages in depth is 0.5 cm. The color bar is tHb in the unit of micromoles per liter.

For each time point, coregistered US images and DOT data, i.e., images of the same regions of the subject, were acquired at the tumor site and the mirror position of the contralateral breast. The contralateral data were used as the reference to compute the normalized perturbation caused by tumor. The weight matrix computed from Born approximation was used to link the unknown tumor and background absorption distribution to the measured perturbation. A two-step image reconstruction using truncated Moore-Penrose pseudoinverse solution as the initial estimate of the optical properties of the tumor and a Newton optimization for inversion is used for imaging reconstruction. Since DOT has a much lower spatial resolution than that of US, for DOT reconstruction, we use two to three times larger size in spatial dimension than that identified by coregistered US. Further, because DOT depth resolution is not as good as US, we use the lesion depth range identified by coregistered US to define DOT reconstruction depth. When US-guided DOT was used for assessing treatment response, the same region of interest was used for DOT reconstruction for all time points, therefore, DOT reconstruction was not affected by changes of tumor sizes in the US images. tHb maps are computed from optical absorption distributions obtained from four wavelengths using extinction coefficients reported in the literature and the maximum tHb was used to quantitatively characterize the tumor at each time point.

In the US images, the tumor manifest as an oval mass with well-defined margins, measured as having a maximum diameter of 2.02 cm before treatment, decreased mildly to 1.49 cm at the completion of cycle 1, but was unchanged in sizes from the end of cycle 2 to before surgery. The measured tHb reduced from 83.3 mol/L measured before treatment to 69.0, 55.3, 37.9 mol/L measured before completion of cycle 1, cycle 2, and cycle 3. A reduction of 17.2%, 33.6%, 54.5% occurred at the end of cycle 1, 2, and 3, respectively. The hemoglobin level remains unchanged to the end of the treatment before surgery. This patient had a complete pathologic response with no residual tumor, having an MP grade of 5. US showed a substantial decrease from baseline to the end of cycle 1, with more subtle size reduction during the remainder of neoadjuvant treatment. US-guided NIR DOT shows a progressive decline in tHb concentration during the first three cycles, which correlated with a complete pathologic response of MP grade of 5. Note that the tumor tHb content did not completely disappear before surgery, which was often due to reasons such as treatment induced inflammatory changes and microphages.

When introducing elements of aspects of the invention or the embodiments thereof, the articles "a," "an," "the," and "said" are intended to mean that there are one or more of the elements. The terms "comprising," "including," and "having" are intended to be inclusive and mean that there may be additional elements other than the listed elements.

Although described in connection with an exemplary computing system environment, embodiments of the invention are operational with numerous other general purpose or special purpose computing system environments or configurations. The computing system environment is not intended to suggest any limitation as to the scope of use or functionality of any aspect of the invention.

Embodiments of the invention may be described in the general context of computer-executable instructions, such as program modules, executed by one or more computers or other devices. The computer-executable instructions may be organized into one or more computer-executable components or modules. Generally, program modules include, but are not limited to, routines, programs, objects, components, and data structures that perform particular tasks or implement particular abstract data types. Aspects of the invention may be implemented with any number and organization of such components or modules. For example, aspects of the invention are not limited to the specific computer-executable instructions or the specific components or modules illustrated in the figures and described herein. Other embodiments of the invention may include different computer-executable instructions or components having more or less functionality than illustrated and described herein. Aspects of the invention may also be practiced in distributed computing environments where tasks are performed by remote processing devices that are linked through a communications network. In a distributed computing environment, program modules may be located in both local and remote computer storage media including memory storage devices.

While exemplary embodiments of components, assemblies and systems are described, variations of the components, assemblies and systems are possible to achieve similar advantages and effects. Specifically, the shape and the geometry of the components and assemblies, and the relative locations of the components in the assembly, may be varied from that described and depicted without departing from inventive concepts described. In addition, in certain embodiments certain components in the assemblies described may be omitted to accommodate particular applications and installations, while still providing improved systems.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A compact diffuse optical tomography (DOT) system for generating a functional image of a lesion region of a subject, comprising:
   a source subsystem including:
      a plurality of laser diodes configured to generate near-infrared (NIR) optical waves; and
      a laser diode driver board configured to drive the plurality of laser diodes;
   a probe configured to emit the optical waves generated by the source subsystem toward the lesion region and configured to detect optical waves reflected by the lesion region;
   a detection subsystem including:
      a miniaturized detection board including a photomultiplier tube (PMT), wherein the PMT has a plurality of channels and configured to convert the optical waves detected by the probe to electrical signals, and the miniaturized detection board further includes a combined board formed as one single board and including:
         a frequency mixer configured to mix the electrical signals with reference signals to derive mixed signals;
         a second-stage amplifier configured to amplify the mixed signals to derive amplified signals; and
         a bandpass filter configured to filter the amplified signals to derive electrical signals of a selected frequency outputted by the miniaturized detection board; and
      a miniaturized data acquisition board configured to convert the electrical signals outputted by the miniaturized detection board to digital signals, and to output the digital signals from the detection subsystem; and
   a computing device separate from the source subsystem, the probe, and the detection subsystem, the computing device configured to:
      receive the digital signals sent from the detection subsystem, the digital signals comprising lesion functional data from the lesion region of the subject and reference functional data from a healthy tissue region of the subject;
      reconstruct the functional image of the lesion region based on the digital signals by:
         transforming the lesion functional data and the reference functional data to produce perturbation data;
         generating a preliminary estimate of the functional image by applying a truncated pseudoinverse matrix of a weight matrix to the perturbation data; and
         generating the functional image by iteratively optimizing successive estimates of the functional image regularized by the preliminary estimate of the functional image weighted by a regularization parameter; and
      display the functional image.

2. The compact DOT system of claim 1, wherein the miniaturized data acquisition board includes a three-layered board having a top layer, a bottom layer, and a ground layer disposed between the top and bottom layers, and the ground layer is configured to reduce coherent interference between electrical signals carried on the top layer and electrical signals carried on the bottom layer.

3. The compact DOT system of claim 2, wherein the three-layered board is a printed circuit board and further includes grounded through-holes placed on sides of traces of the top layer and on sides of traces of the bottom layer, and the traces of the top layer and the traces of the bottom layer are configured to carry signals.

4. The compact DOT system of claim 1, wherein the second-stage amplifier has an adjustable gain and is configured to adjust the gain to control a dynamic range of the detection subsystem.

5. The compact DOT system of claim 1, further including an ultrasound imaging device configured to localize the lesion region, and the compact DOT system is configured to generate the functional image of the lesion region.

6. The compact DOT system of claim 1, wherein the miniaturized data acquisition board includes a field programmable gate array (FPGA) configured to control a gain of the PMT.

7. The compact DOT system of claim 1, wherein the miniaturized data acquisition board includes an FPGA, and the laser diode driver board further includes one or more optical switches configured to multiplex the optical waves generated by the plurality of laser diodes, and the FPGA is configured to control the one or more optical switches.

8. A compact diffuse optical tomography (DOT) system for generating a functional image of a lesion region of a subject, comprising:
a source subsystem including:
a plurality of laser diodes configured to generate near-infrared (NIR) optical waves; and
a laser diode driver board configured to drive the plurality of laser diodes;
a probe configured to emit the optical waves generated by the source subsystem toward the lesion region and configured to detect optical waves reflected by the lesion region;
a detection subsystem including:
a miniaturized detection board including a photomultiplier tube (PMT) having a plurality of channels and configured to convert the optical waves detected by the probe to electrical signals; and
a miniaturized data acquisition board configured to convert electrical signals outputted by the miniaturized detection board to digital signals, and to output the digital signals from the detection subsystem; and
a computing device separate from the source subsystem, the probe, and the detection subsystem, the computing device configured to:
receive the digital signals sent from the detection subsystem, the digital signals comprising lesion functional data from the lesion region of the subject and reference functional data from a healthy tissue region of the subject;
reconstruct the functional image of the lesion region based on the digital signals by:
transforming the lesion functional data and the reference functional data to produce perturbation data;
generating a preliminary estimate of the functional image by applying a truncated pseudoinverse matrix of a weight matrix to the perturbation data; and generating the functional image by iteratively optimizing successive estimates of the functional image regularized by the preliminary estimate of the functional image weighted by a regularization parameter; and
display the functional image.

9. The compact DOT system of claim 8, wherein the probe includes a plurality of source electrodes and a plurality of detector electrodes disposed on an opposite side of the probe from the plurality of source electrodes.

10. The compact DOT system of claim 9, wherein the plurality of source electrodes are separated from the plurality of detector electrodes by a distance from approximately 3.2 cm to approximately 8.5 cm.

11. The compact DOT system of claim 8, wherein the source subsystem is configured to generate optical waves at four optical wavelengths in a range from approximately 730 nm to approximately 830 nm.

12. The compact DOT system of claim 8, wherein the computing device is configured reconstruct the functional image by:
providing an initial estimate of the functional image through a pseudoinverse; and
reconstructing the functional image through optimization using the provided initial estimate.

13. The compact DOT system of claim 12, wherein providing an initial estimate further includes providing an initial estimate of the functional image through Moore-Penrose pseudoinverse, and reconstructing the functional image further includes reconstructing the functional image through at least one of a Conjugate Gradient optimization and a Newton optimization for inversion using the provided initial estimate.

14. The compact DOT system of claim 8, wherein the computing device is a portable computer and communicates with the detection subsystem via a universal series bus port.

15. The compact DOT system of claim 8, further including an ultrasound imaging device configured to localize the lesion region, and the compact DOT system is configured to generate the functional image of the lesion region.

16. A compact diffuse optical tomography (DOT) system for generating a functional image of a lesion region of a subject, comprising:
a source subsystem including:
a plurality of laser diodes configured to generate near-infrared (NIR) optical waves; and
a laser diode driver board configured to drive the plurality of laser diodes, wherein the laser diode driver board includes one or more optical switches configured to multiplex the optical waves generated by the plurality of laser diodes;
a probe configured to emit the optical waves generated by the source subsystem toward the lesion region and configured to detect optical waves reflected by the lesion region;
a detection subsystem including:
a miniaturized detection board including a photomultiplier tube (PMT) having a plurality of channels and configured to convert the optical waves detected by the probe to electrical signals; and
a miniaturized data acquisition board configured to convert electrical signals outputted by the miniaturized detection board to digital signals, and to output the digital signals from the detection subsystem; and
a computing device separate from the source subsystem, the probe, and the detection subsystem, the computing device configured to:

receive the digital signals sent from the detection subsystem, the digital signals comprising lesion functional data from the lesion region of the subject and reference functional data from a healthy tissue region of the subject;

reconstruct the functional image of the lesion region based on the digital signals by:
- transforming the lesion functional data and the reference functional data to produce perturbation data;
- generating a preliminary estimate of the functional image by applying a truncated pseudoinverse matrix of a weight matrix to the perturbation data; and
- generating the functional image by iteratively optimizing successive estimates of the functional image regularized by the preliminary estimate of the functional image weighted by a regularization parameter; and display the functional image.

17. The compact DOT system of claim 16, wherein the laser diode driver board is configured to provide current to drive the plurality of laser diodes and further includes a plurality of bias-tees each configured to provide a radio frequency input to one of the plurality of laser diodes.

18. The compact DOT system of claim 16, wherein the source subsystem further includes control modules configured to control temperatures of the plurality of the laser diodes and a cooling system controlled by the control modules and configured to cool the plurality of laser diodes.

19. The compact DOT system of claim 16, further including an ultrasound imaging device configured to localize the lesion region, and the compact DOT system is configured to generate the functional image of the lesion region.

20. The compact DOT system of claim 16, wherein the miniaturized data acquisition board includes a field programmable gate array configured to control the one or more optical switches.

\* \* \* \* \*